(12) United States Patent
Yin et al.

(10) Patent No.: US 7,351,817 B2
(45) Date of Patent: Apr. 1, 2008

(54) **NUCLEIC ACIDS FROM RICE CONFERRING RESISTANCE TO BACTERIAL BLIGHT DISEASE CAUSED BY *XANTHOMONAS* SPP**

(75) Inventors: Zhong Chao Yin, Singapore (SG); Guo-Liang Wang, Columbus, OH (US); Dong Sheng Tian, Singapore (SG); Ke Yu Gu, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 10/568,081

(22) PCT Filed: Aug. 13, 2003

(86) PCT No.: PCT/SG03/00191

§ 371 (c)(1),
(2), (4) Date: Feb. 13, 2006

(87) PCT Pub. No.: WO2005/017158

PCT Pub. Date: Feb. 24, 2005

(65) Prior Publication Data

US 2006/0143734 A1    Jun. 29, 2006

(51) Int. Cl.
*C07H 21/04* (2006.01)
*C12N 5/10* (2006.01)
*C12N 15/74* (2006.01)

(52) U.S. Cl. .................. 536/23.6; 435/320.1; 435/419; 435/471

(58) Field of Classification Search ..................... None
See application file for complete search history.

(56) References Cited

FOREIGN PATENT DOCUMENTS

| | | |
|---|---|---|
| CN | 1241630 A | 1/2000 |
| WO | WO 99/09151 A | 2/1999 |

OTHER PUBLICATIONS

Zhang et al 1999, Nature Biotech. 17:1021-1024.*
Fourgoux-Nicol et al 1999, Plant Molecular Biology 40 :857-872.*
Falcon-Perez JM et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Sasaki et al. 2001, GenBank Accession No. AP003623.*
Genbank Accession No. AC079889, Buell, C.R. et al., "*Oryza sativa* chromosome 3 BAC OSJNBa0092M19 genomic sequence, complete sequence", Mar. 22, 2003.
Genbank Accession No. AB023482, Sasaki, T., et al., "*Oryza sativa* (japonica cultivar-group) genomic DNA, chromosome 6, clone P0680A03" May 25, 2002.

* cited by examiner

*Primary Examiner*—Aswin Mehta
*Assistant Examiner*—Li Zheng
(74) *Attorney, Agent, or Firm*—Rothwell, Figg, Ernst & Manbeck, P.C.

(57) ABSTRACT

The present invention provides plants, plant cells and methods of making transgenic plants or plant cells, wherein the plants or cells are resistant to bacterial blight. The invention provides isolated nucleic acid sequences comprising SEQ ID NO: 1 or fragments thereof which provide a plant with resistance to bacterial blight disease when transfected into the plant.

8 Claims, 9 Drawing Sheets

14 DPI with Xoo PXO99

```
IRBB31   CACTGGATCCAAACACCACCTAAGGT-------------TTTCTTGTGTACTTGTGTGAATTGTGGTTGACTACGACTACTAGTGCTATA
IR24     CCCTGGATCCAAACGCCACCTAAGGTtttcttgtacttgtgaattgtggTTTCTTGTGTACTTGTGTGAATTGTGGTTGACTACGACTAGTGCTATA
                                  •              •                              ••••••

IRBB31   AATAGAAGAGAGACCCATAGAGAGCATCAGAGACCAAAGTACTCCTAAAAGACAGCCACACACACTGAGAGACACCCAATGGCGGATTG
IR24     AATA---GAAGAGACCAATAGAGAGCATCAGAGACCAAAGTACTCCTAAAAGACAGCCACACAC---TGAGAGACACCCAATGGCGGATTG
cDNA 1   AATA---GAAGAAGTGCCTCCAATGGCGGATTG
              +1
```

Figure 9

```
                        SEQUENCE LISTING

<160> NUMBER OF SEQ ID NOS: 52

<210> SEQ ID NO 1
<211> LENGTH: 5198
<212> TYPE: DNA
<213> ORGANISM: Oryza sativa
<220> FEATURE:
<221> NAME/KEY: Dominant (Resistant) allele of the Xa31 genomic clone
      from IRBB31
<222> LOCATION: (1)..(5198)
<223> OTHER INFORMATION:

<400> SEQUENCE: 1
tgcatgagga ctgaacgcct gaaccagctg cagtgccatc gatccacgag tacggtacag      60
ccatgcgtta gtgagaaccg aaaagggaa aaaaaaaaa acctcagcca caaagcacaa       120
tttttttttt agaaatacac tacagcatgt ctcgctatct gactctcgct atctgacttg     180
tatattgctt aacacttaaa cggacataga cgttgttatc aatggatatg tcgtctacca     240
ctaaaataat aattagcctt aaatacgagc gtttatattt acaatgtgca ttaggttata    300
ttttgaaaca tataatttag ctttgattta tcctatattc tagaaaaaaa ataataatta    360
gtagcaagta taaacatcat gaacatattt ttcttctaac tctacagttt taacaactta    420
taggcaaaac ttttgaattt ataaaagtga gatggagtat tcataaaaca cacatttctt    480
gccctctaat accaccttca tcaatttgtt aatttgttag cgtatattat tatgatgcag    540
tgtttcttac tcagtatccc aaaaataaat ctaaaaacac accaaaagga tattttaaag    600
gtacgacatt gatacaactt taagtattgg attaattgct taaaaaaatc tcacgttcta    660
aataatctct aagtagtata caaatattca aaaaaaggtt ttacgggcta aattagcaag    720
cgtgccaata gacacgctga ttttctagtc tgatgataat gcggttcatt tccatttccg    780
tttggtacag ccgtaacttt agcttcatct ttttcgaggc tgcagctgaa ccaaacagtt    840
ttagctccat cgaagaaagg agttatactg attggaatgc tctcacagta aaaaaaacaa    900
ggaagtagag ctggattta dacagttcta caagaagtta gaactctacc aaaattggaa    960
```

```
ttttggatga tggtctttta aaaactcgat tgcaggaata aaattttacg gcttgaaact    1020
tacaaaatga ttagaaaaga taacatgcct cagcgatttg taaaaaagtg aacaaataaa    1080
aatctacaat accactaaac tattgcttta ttttggggac attgcttacc attgaaaaaa    1140
caactaaccg taaatacgaa cacccatatc aaatatacta tcactgataa aataatcaat    1200
tgtaaattca agcacacata ttagtatagt actttaactc gattggatag aagaaaccta    1260
actaatttaa gctatgcctc acaacaaaaa ggtataaatt ttttaaggct tcttttttt    1320 tcttgcgttt gctagtttat gcttttaaga tgtttatacc ttttactccc ctcattcact    1380
gtttaaatac aatgggaatt agtgaaatca atgagagttc aaacttcgaa acactgaata    1440
catgttattt tggattgaaa tcaaatcgaa tcagtcaaat tcaaatagga ggaggaacat    1500
aggcattctt cctttcttca gcgggcacca ttgaattcag atactgcttc gcctagtctc    1560
tgtccaagac tccacatttt ctgatggtga tggggaactc tgaaactata ggaggaagaa    1620
taaaatgaag aatgcagaaa tgaatagtaa tttgtgtttt ttaattcttc ttcaattcca    1680
ccttaggatc caacttcagt ccaaatccaa agtaatgcaa ctgccactag atcaggctag    1740
agcttcaaat tcaactccaa aaacctccgt aaagtggcac acacagagga aaaatcctgg    1800
attcgtcact gcccatcaac atctgctttc gcctcccaat tcctgctttc tgaaatctgc    1860
tttcgccgaa ttcatgcctt cttgaattat gctttcttag accctcttta gatgggacta    1920
aaacttttac tctctatcac atcggatgtt tggacactaa ttataaatat taaacgtaga    1980
ctattaataa aacccatcta taatcttgta ttaattcgcg agacgaatct attgagccta    2040
attaatccat gattagccta tgtgatgcta taataaacat tctctaatta taaattaatt    2100
gggcttaaaa aatttgtctc gcgtattagc tttcatttat ataattagtt ttataaatag    2160
tctatattta atactctaaa ttagtgtcta aatacaggga ctaaagttaa gtcactggat    2220
ccaaacacca cctaaggttt tcttgtgtac ttgtgaattg tggttgacta cgactactag    2280
tgctataaat agaagaagag acccatagag agcatcagag caaagtactc ctaaaagaca    2340
gccacacaca ctgagacacc caagaagctg cctccaatgg cggattgggc gatgcaccac    2400
tacctcctac tagccaacca gcaacgccac cgagccctcg ccgacgtcgc cgtccgccgc    2460
cgccagctgc cctcgactc cggcgcgtc ttcatgctcc tcggcgccgt catcctcatg    2520
cacatgctca ccactaccgg cggcggagca tcgtccggct gcacccgcgg cgccgaacct    2580
tgcgtcgccc tcctcctgtg gctgctcggc gcggcgctcg ccatgctgtc gctcgtcgcc    2640
ggccgattcc ccgttctcgc tgccgccatt gctgaggagc tcggtgatca cctgcttggt    2700
ggtctctggt ctctctagtt ctcctccgtg tccggtggtc atcttcttct ccgtgctttt    2760
gctctggagt tgagtacgga tctgtgtgta ctgcattctt gcttaattag tgccctacac    2820
gttatgcttt cgaaacatca tctttttca gtatagttca ataaatttca gctcaaattt    2880
gtcctccaag acgagttctc catccaaacg aaacttatgg tgttccgttg tttgggccga    2940
ttttatatgt tggaaatgta cagacttcat agtactgtgt ttcttttttg gaataagttc    3000
accagaggtt ccttaactta acggcgatat ttttttaggt cctttaacca caaaaccaga    3060
aatgtgcacc cctaaacttt cacaatccgt gcacaagagg tcctatggca gtacgtgg     3120 gtggtttcgc tgacgtgaca tcctagtcag caaaaataaa taaataagta agtggggccc    3180
atatgtaagt gagagaaaac gatgcgggcc ccacatccct tcttttttccc cctttcttct    3240 cctctcgtct tcttcgacgg ggcgagacgg gcggggcaac ggccggcgag agtggcggcg    3300
```

```
gcggcggagg gcgagcgcgg ccgcggcaag cgaagcaggc aggagcgggg cgacggccgg    3360
cgagaacggc ggcggactga gggcgaccgc ggcgggaggg agggacggga ttcgagacgg    3420
gctcctgctc tggaagggga tccccgcggc cgacggagat gtcgccgccg gtggcggagg    3480
agggcgcgaa gggggcgagg aggagggagg acgcaatcca gatggcgacg gacgtgagca    3540
cacaaaactg aaggtgcggt cgaatgccga gcgtgccaag gccggacctg agcttgccgg    3600
ggatgctcat gaggtcgaag aacggcaagt cgccaggctt ggactgcact ggccttagct    3660 tccccctccca cagcacgaac tgtggcgcgt tgaggtcccc gaacacgaaa tcgtccttga    3720
gcccgctgtc cacctgcgcg cccaatccaa gcaccaccat tccattcatg tcctcgccgc    3780
cgtgagagaa tcagaagggg tgggagagga ggaggagaat ggagaaggga gcaagaaggc    3840
gtacggccat ggtgaggacg gggtcggaag gctggaagct gttgggcccc tcctcccaga    3900
gatagccctc gttggcgcgc tcgatggtgg tgatgttgcc gccgaggcga gcgcgggcct    3960
ccgtgacgag cacgtcgccg acgccgtgct tggtggccag cgcctgcacg gtgcagagcc    4020
cgttgatgcc cgtcgccacc gcgctcgcct accccgccg ctcctgcctg catcacctgc    4080
cgccgccgcg ctcgcccgcc gccggctgtc gccccgcccg tctcggctcg tcaaagaaga    4140
cgagagaaga gaagaaaata aaggagaatt gagaagaaag gggaagaaag aagggatgtg    4200
gggccacacc gttttctcta actacatgtg gccccacat actttattta tttattttg     4260 ctgactagga tgccacgtca gtgaaaccgc tcacgtatac tgccatagga cctttgtgc     4320 atggtttgtg aaagtttagg ggtgcacatt tctggtttta tggttaaggg atcgctgtta    4380
agttgaggga ccaccggtga acttattcct tcttttttg tttgtttttt ttttcttttt     4440
gaaatgagtg tactgtgttc tttggagttt agtgggctgc gttgtcgcta ccagcaaat     4500 agagaacggc ccaaccagac aagcaatctt cttacaagca gcccacttat gacaaatctg    4560
gaccatccgt tggcaattca acgacaaata tgttatcctc gtcgatctca agcagcccac    4620
ttatgacaaa tatgcagttt gatttgtttt tggttttcgc ttgtgaagcc ccgcgagat     4680 tcgagaagag gaggtggtgg catggtatac ggacggcaac acggtcatga ggagcgagca    4740
gaatcccagc gctgccacga gtgacgacaa cgccgtcacc accagcagca gcagcagcac    4800
gaccgacgcc gacaagaagg cctcagcctc accgttcgag ccgctccgcg cctccgcccc    4860
gcctgtcatt gctccggccg ccgccgccc cgctctgtct ccgtccttct gttctgccgc    4920
cgctccaccc tgccatcgcc cgctccggcc gccacccacc ccgctccgca ggcttgagag    4980
agagaagagg gagagagagg atagagagag ggggaataag agaggagggt tgtgaggatg    5040
atgtgtgggt ccacatgggc tcaccatttt ttattatgta tgtttgcaac tgatatgtgg    5100
gtcccacggt ttttattatt tttttcggat ctaattgcca cgtaggctcc acgttaatga    5160
cacgctggac aaagacctag tcaaagagag ccacctag                            5198
```

<210> SEQ ID NO 2
<211> LENGTH: 5131
<212> TYPE: DNA
<213> ORGANISM: Oryza sativa
<220> FEATURE:
<221> NAME/KEY: Recessive (susceptible) allele of the xa31 genomic clone
    from IR24
<222> LOCATION: (1)..(5131)
<223> OTHER INFORMATION:

<400> SEQUENCE: 2

```
aggtggctct ctttgactag gtctttgtcc agcgtgtcat taacgtggag cctacgtggc      60
```

-continued

| | | |
|---|---|---|
| aattagatcc gaaaaaaata ataaaaacca tgggacccac atatcagttg caaacataca | 120 |
| taataaaaaa tggtgagccc atgtggaccc acacatcatc ctcacaaccc tcttctctta | 180 |
| ttcccctct ctctatcctc tctctccctc ttctctctct caagcctgcg gagcggggtg | 240 |
| ggtggcggcc ggagcgggcg atggcagggt ggagcggcgg cagaacagaa ggacggagac | 300 |
| agagcggggc gggcggcggc cggagcaatg acaggcgggg cggaggcgcg gagcggctcg | 360 |
| aacggtgagg ctgaggcctt cttgtcgcg tcggtcgtgc tgctgctgct gctggtggtg | 420 |
| acggcgttgt cgtcactcgt ggcagcgctg ggattctgct cgctcctcat gaccgtgttg | 480 |
| ccgtccgtat accatgccac cacctcctct tctcgaatct cgcgggggct tcacaagcga | 540 |
| aaaccaaaaa caaatcaaac tgcatatttg tcataagtgg gctgcttgag atcgaggagg | 600 |
| ataacatatt tgtcgttgaa ttgccaacgg atggtccaga tttgtcataa gtgggctgct | 660 |
| tgtaagaaga ttgcttgtct ggttgggccg ttctctattt gctcggtagc gacaacgcag | 720 |
| cccactaaac tccaaagaac acagtacact catttcaaaa agaaaaaaaa caaacaaaaa | 780 |
| aagaaggaat aagttcaccg gaggtccctc aacttaacag cgatcccttaa accataaaac | 840 |
| cagaaatgtg caccctaaa cttcacaaa ccatgcacaa aaggtcctat ggcagtatac | 900 |
| gtgagcggtt tcgctgacgt ggcatcctag ttagcaaaaa taaataaata aagtatgtgg | 960 |
| ggcccacatg tagttagaga aaacggtgtg ggccccacat cccttcttc ttcccctttc | 1020 |
| ttctcaattc tcctttattt tcttctcttc tctcgtcttc tttaacgggc cgagacgggc | 1080 |
| ggggcgacag ccggcggcgg gcgagcgcgg cggcggcagg tgatgcaggc aggagcggcg | 1140 |
| ggggtaggcg agcgcggtgg cgacgggcat caacgggctc tgcaccgtgc aggcgctggc | 1200 |
| caccaagcac ggcgtcggcg acgtgctcgt cacggaggcc cgcgcccgcc tcggcggcaa | 1260 |
| catcaccacc atcgagcgcg ccaacgaggg ctatctctgg gaggaggggc ccaacagctt | 1320 |
| ccaaccttcc gaccccgtcc tcaccatggc cgtacgcctt cttgctccct tctccattct | 1380 |
| cctcctcctc tcccacccct tctgattctc tcacggcggc gaggacatga atggaatggt | 1440 |
| ggtgcttgga ttgggcgcgc aggtggacag cgggctcaag gacgatttcg tgttcgggga | 1500 |
| cctcaacgcg ccacagttcg tgctgtggga ggggaagcta aggccagtgc agtccaagcc | 1560 |
| tggcgacttg ccgttcttcg acctcatgag catccccggc aagctcaggt ccggccttgg | 1620 |
| cacgctcggc attcgaccgc accttcagtt ttgtgtgctc acgtctgtcg ccatctggat | 1680 |
| tgcgtcctcc ctcctcctcg ccccttcac gccctcctcc gccaccagcg gcgacatctc | 1740 |
| cgtcggccgc ggggatcccc ttccagagca ggagcccgtc tcgaatcccg tccctacctc | 1800 |
| ccgccgcgt cgccctcagt ccgccgccgt tctcgccggc cgtcgccccg ctcctgcctg | 1860 |
| cttcgcttgc cgcggccgcg ctcgccctcc gccgccgccg ccactcgccg gccgtcgccc | 1920 |
| cgcccgtctc gccccgtcga agaagacgag aggagaagaa aggggaaaa agaagggatg | 1980 |
| tggggcccgc atcgttttct ctcacttaca tatgggcccc acttactat ttatttattt | 2040 |
| ttgctgacta ggatgtcacg tcagcgaaac cacccacgta tactgccata ggacctcttg | 2100 |
| tgcacggatt gtgaaagttt aggggtgcac atttctggtt ttgtggttaa aggacctaaa | 2160 |
| aaaatatcgc cgttaagtta aggaacctct ggtgaactta ttccaaaaaa gaaacacagt | 2220 |
| actatgaagt ctgtacattt ccaacatata aaatcggccc aaacaacgga acaccataag | 2280 |
| tttcgtttgg atggagaact cgtcttggag gacaaatttg agctgaaatt tattgaacta | 2340 |
| tactgaaaaa agatgatgtt tcgaaagcat aacgtgtagg gcactaatta agcaagaatg | 2400 |
| cagtacacac agatccgtac tcaactccag agcaaaagca cggagaagaa gatgaccacc | 2460 |

```
ggacacggag gagaactaga gagaccagag accaccaagc aggtgatcac cgagctcctc    2520
agcaatggcg gcagcgagaa cggggaatcg gccggcgacg agcgacagca tggcgagcgc    2580
cgcgccgagc agccacagga ggagggcgac gcaaggttcg gcgccgcggg tgcagccgga    2640
cgatgctccg ccgccggtag tggtgagcat gtgcatgagg atgacggcgc cgaggagcat    2700
gaagacgcgg ccggagtcga ggagcagctg gcggcggcgg acggcgacgt cggcgagggc    2760
tcggtggcgt tgctggttgg ctagtaggag gtagtggtgc atcgcccaat ccgccattgg    2820
aggcagcttc ttgggtgtct cagtgtgtgt ggctgtcttt taggagtact ttgctctgat    2880
gctctctatt ggtctcttct atttatagca ctcgtagtcg tagtcaacca caattcacaa    2940
gtacacaaga aaccacaatt cacaagtaca caagaaaacc ttaggtggcg tttggatcca    3000
gggacttaac tttagtccct gtatttagac actaatttag agtattaaat atagactatt    3060
tataaaacta attacataaa tgaaagctaa tacgcgagac aaatttttta agcccaatta    3120
atttataatt agagaatgtt tattatagca tcacataggc taatcatgga ttaattaggc    3180
tcaatagatt cgtcacgcga attaatacaa gattatagat gggttttatt aatagtctac    3240
gtttaatatt tataattagt gtccaaacat ccgatgtgat agagagtaaa agttttagtc    3300
tcatctaaag agggtctaag aaagcataat tcaagaaggc atgaattcgg cgaaagcaga    3360
tttcagaaag caggaattgg gaggcgaaag cagatgttga tgggcagtga cgaatccagg    3420 attttttcctc tgtgtgtgcc actttacgga ggtttttgga gttgaatttg aagctctagc    3480
ctgatctagt ggcagttgca ttactttgga tttggactga agttggatcc taaggtggaa    3540
ttgaagaaga attaaaaaac acaaattact attcatttct gcattcttca ttttattctt    3600
cctcctatag tttcagagtt ccccatcacc atcagaaaat gtggagtctt ggacagagac    3660
taggcgaagc agtatctgaa ttcaatggtg cccgctgaag aaaggaagaa tgcctatgtt    3720
cctcctccta tttgaatttg actgattcga tttgatttca atccaaaata acatgtattc    3780
agtgtttcga agtttgaact ctcattgatt tcactaattc ccattgtatt taaacagtga    3840
atgaggggag taaaaagtat aaacatctta aaagcataaa ctagcaaacg caagaaaaaa    3900
aaagaagcct taaaaaattt ataccttttt gttgtgaggc atagcttaaa ttagttaggt    3960
ttcttctatc caatcgagtt aaagtactat actaatatgt gtgcttgaat ttacaattga    4020
ttattttatc agtgatagta tatttgacat gggtgttcgt atttacggtt agttgttttt    4080
tcaatggtaa gcaatgtccc caaaataaag caatagttta gtggtattgt agattttttat    4140 ttgttcactt ttttacaaat cgctgaggca tgttatcttt tctaatcatt ttgtaagttt    4200
caagccgtaa aatttttattc ctgcaatcga gttttttaaaa gaccatcatc caaaattcca    4260
attaactatc cgtttggtag agttctaact tcttatagaa ctgtctaaaa tccagctcta    4320
cttccttgtt ttttttaact gtgagcattc caatcagtat aactcctttc ttcgatggag    4380
ctaaaactgt ttggttcagc tgcagcctcg aaaaagatga agctaaagtt acggctgtac    4440
caaacggaaa tggaaatgaa ccgcattatc atcagactag aaaatcagcg tgtctattgg    4500
cacgcttgct aatttagccc gtaaaacctt ttttgaata tttgtatact acttagagat    4560
tatttagaac gtgagatttt ttaagcaatt aatccaatac ttaaagttgt atcaatgtcg    4620 taccttttaaa atatcctttt ggtgtgtttt tagatttatt tttgggatac tgagtaagaa    4680
acactgcatc ataataatat acgctaacaa attaacaaat tgatgaaggt ggtattagag    4740
ggcaagaaat gtgtgttttta tgaatactcc atctcacttt tataaattca aaagtttgc    4800
```

-continued

```
ctataagttg ttaaaactgt agagttagaa gaaaaatatg ttcatgatgt ttatacttgc      4860
tactaattat tattttttc tagaatatag gataaatcaa agctaaatta tatgtttcaa       4920 aatataaccct aatgcacatt gtaaaataaa acgctcgtat ttaaggctaa ttattctttt    4980
agtggtagac gacatatcta ttgataacga cgtctatgtc cgtttaagtg ttaagcaata     5040
tacaagtcag atagcgagag tcagatagcg agacatgctg tagtgtattt ctaaaaaaaa     5100
aattgcgctt tgtggctgag gttttttttt t                                    5131
```

<210> SEQ ID NO 3
<211> LENGTH: 593
<212> TYPE: DNA
<213> ORGANISM: Oryza sativa
<220> FEATURE:
<221> NAME/KEY: cDNA 1 from IRBB31
<222> LOCATION: (1)..(593)
<223> OTHER INFORMATION:

<400> SEQUENCE: 3

```
agagcaaagt actcctaaaa gacagccaca cacactgaga cacccaagaa gctgcctcca      60
atggcggatt gggcgatgca ccactacctc ctactagcca accagcaacg ccaccgagcc     120
ctcgccgacg tcgccgtccg ccgccgccag ctgctcctcg actccggccg cgtcttcatg     180
ctcctcggcg ccgtcatcct catgcacatg ctcaccacta ccggcggcgg agcatcgtcc     240
ggctgcaccc gcggcgccga accttgcgtc gccctcctcc tgtggctgct cggcgcggcg     300
ctcgccatgc tgtcgctcgt cgccggccga ttccccgttc tcgctgccgc cattgctgag     360
gagctcggtg atcacctgct tggtggtctc tggtctctct agttctcctc cgtgtccggt     420
ggtcatcttc ttctccgtgc ttttgctctg gagttgagta cggatctgtg tgtactgcat     480
tcttgcttaa ttagtgccct acacgttatg ctttcgaaac atcatctttt ttcagtatag    540
ttcaataaat ttcagctcaa atttgtcctc caaaaaaaaa aaaaaaaaaa aaa            593
```

<210> SEQ ID NO 4
<211> LENGTH: 585
<212> TYPE: DNA
<213> ORGANISM: Oryza sativa
<220> FEATURE:
<221> NAME/KEY: cDNA 3 from IR24
<222> LOCATION: (1)..(585)
<223> OTHER INFORMATION:

<400> SEQUENCE: 4

```
agagcaaagt actcctaaaa gacagccaca cacactgaga cacccaagaa gctgcctcca      60
atggcggatt gggcgatgca ccactacctc ctactagcca accagcaacg ccaccgagcc     120
ctcgccgacg tcgccgtccg ccgccgccag ctgctcctcg actccggccg cgtcttcatg     180
ctcctcggcg ccgtcatcct catgcacatg ctcaccacta ccggcggcgg agcatcgtcc     240
ggctgcaccc gcggcgccga accttgcgtc gccctcctcc tgtggctgct cggcgcggcg     300
ctcgccatgc tgtcgctcgt cgccggccga ttccccgttc tcgctgccgc cattgctgag     360
gagctcggtg atcacctgct tggtggtctc tggtctctct agttctcctc cgtgtccggt     420
ggtcatcttc ttctccgtgc ttttgctctg gagttgagta cggatctgtg tgtactgcat     480
tcttgcttaa ttagtgccct acacgttatg ctttcgaaac atcatctttt ttcagtatag    540
ttcaataaat ttcagctcaa atttgtcctc caaaaaaaaa aaaaa                     585
```

<210> SEQ ID NO 5
<211> LENGTH: 113

```
<212> TYPE: PRT
<213> ORGANISM: Oryza sativa
<220> FEATURE:
<221> NAME/KEY: Polypeptide
<222> LOCATION: (1)..(113)
<223> OTHER INFORMATION:

<400> SEQUENCE: 5
```

Met Ala Asp Trp Ala Met His His Tyr Leu Leu Leu Ala Asn Gln Gln
1               5                   10                  15

Arg His Arg Ala Leu Ala Asp Val Ala Val Arg Arg Gln Leu Leu
            20                  25                  30

Leu Asp Ser Gly Arg Val Phe Met Leu Leu Gly Ala Val Ile Leu Met
            35                  40                  45

His Met Leu Thr Thr Thr Gly Gly Ala Ser Ser Gly Cys Thr Arg
50                      55                  60

Gly Ala Glu Pro Cys Val Ala Leu Leu Leu Trp Leu Leu Gly Ala Ala
65                  70                  75                  80

Leu Ala Met Leu Ser Leu Val Ala Gly Arg Phe Pro Val Leu Ala Ala
                85                  90                  95

Ala Ile Ala Glu Glu Leu Gly Asp His Leu Leu Gly Gly Leu Trp Ser
                100                 105                 110

Leu

```
<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
tagctaaata aaagcaattt tacga                                      25

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
gcccttacat atcgatgttt attg                                       24

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
tgtgcaatgc aggatttcag ttact                                      25

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
tttcacctgc ataatgcaaa agctaa                                     26
```

-continued

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ctgcatccat gccggtggcc g                                    21

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
aaacgtcaca tgaagactcc aattgt                               26

<210> SEQ ID NO 12
<211> LENGTH: 23
<212> TYPE: DNA
<213> ORGANISM: Artificial Sequence
<220> FEATURE:
<223> OTHER INFORMATION: primers

<400> SEQUENCE: 12
agggatgtcg agatgagagc ttc                                  23

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
ggtgtccttc tttacgggcc tcc                                  23

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
gctgtgaagt gccgggtgtc c                                    21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
tggacaggac gatgccggtg g                                    21

<210> SEQ ID NO 16
<211> LENGTH: 23
<212> TYPE: DNA
<213> ORGANISM: Artificial Sequence
<220> FEATURE:

<223> OTHER INFORMATION: primer

<400> SEQUENCE: 16
cccagcaagg ccatatcccg aca                                                    23

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
tccccgcctt cgtctcgccg t                                                      21

<210> SEQ ID NO 18
<211> LENGTH: 30
<212> TYPE: DNA
<213> ORGANISM: Artificial Sequence
<220> FEATURE:
<223> OTHER INFORMATION: oligonucleotide

<400> SEQUENCE: 18
aagcagtggt atcaacgcag agtacgcggg                                             30

<210> SEQ ID NO 19
<211> LENGTH: 57
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (57)..(57)
<223> OTHER INFORMATION: n = a, t, c, or g

<400> SEQUENCE: 19
aagcagtggt atcaacgcag agtactvvvv vvvvvvvvvv vvvvvvvvvv vvvvvvn              57

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
caaccagcaa cgccaccgag cc                                                     22

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
aagcagtggt atcaacgcag agt                                                    23

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22

```
accttgcgtc gccctcctcc tg                                              22

<210> SEQ ID NO 23
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (49)..(49)
<223> OTHER INFORMATION: n= a, t, c, or g
<220> FEATURE:
<221> NAME/KEY: misc_feature
<222> LOCATION: (27)..(27)
<223> OTHER INFORMATION: n= a, t, c, or g

<400> SEQUENCE: 23
tvvvvvvvvv vvvvvvvvvv vvvvvvn                                         27

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
ctcctcagca atggcggcag cga                                             23

<210> SEQ ID NO 25
<211> LENGTH: 45
<212> TYPE: DNA
<213> ORGANISM: Artificial Sequence
<220> FEATURE:
<223> OTHER INFORMATION: primer

<400> SEQUENCE: 25
ctaatacgac tcactatagg gcaagcagtg gtatcaacgc agagt                     45

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
ctaatacgac tcactatagg gc                                              22

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
acacacagat ccgtactcaa ctcc                                            24

<210> SEQ ID NO 28
<211> LENGTH: 38
<212> TYPE: DNA
<213> ORGANISM: Artificial Sequence
<220> FEATURE:
<223> OTHER INFORMATION: primer
```

```
<400> SEQUENCE: 28
gaccacgcgt atcgatgtcg actttttttt tttttttt                                  38

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
gagagcatca gagcaaagta ctcc                                                 24

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
gaccacgcgt atcgatgtcg ac                                                   22

<210> SEQ ID NO 31
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n = a, g, c, or t

<400> SEQUENCE: 31
ntcgaswtsg wgtt                                                            14

<210> SEQ ID NO 32
<211> LENGTH: 16
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n = a, g, c, or t
<220> FEATURE:
<221> NAME/KEY: misc_feature
<222> LOCATION: (11)..(11)
<223> OTHER INFORMATION: n = a, g, c, or t

<400> SEQUENCE: 32
ngtcgaswga nawgaa                                                          16

<210> SEQ ID NO 33
<211> LENGTH: 16
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (5)..(5)
<223> OTHER INFORMATION: n = a, g, c, or t
<220> FEATURE:
<221> NAME/KEY: misc_feature
<222> LOCATION: (10)..(10)
<223> OTHER INFORMATION: n = a, g, c, or t
```

```
<220> FEATURE:
<221> NAME/KEY: misc_feature
<222> LOCATION: (13)..(13)
<223> OTHER INFORMATION: n = a, g, c, or t

<400> SEQUENCE: 33
wgtgnagwan canaga                                                         16

<210> SEQ ID NO 34
<211> LENGTH: 16
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n = a, g, c, or t
<220> FEATURE:
<221> NAME/KEY: misc_feature
<222> LOCATION: (11)..(11)
<223> OTHER INFORMATION: n = a, g, c, or t

<400> SEQUENCE: 34
ngtasaswgt nawcaa                                                         16

<210> SEQ ID NO 35
<211> LENGTH: 16
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (5)..(5)
<223> OTHER INFORMATION: n = a, g, c, or t
<220> FEATURE:
<221> NAME/KEY: misc_feature
<222> LOCATION: (10)..(10)
<223> OTHER INFORMATION: n = a, g, c, or t

<400> SEQUENCE: 35
agwgnagwan cawagg                                                         16

<210> SEQ ID NO 36
<211> LENGTH: 16
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (5)..(5)
<223> OTHER INFORMATION: n = a, g, c, or t
<220> FEATURE:
<221> NAME/KEY: misc_feature
<222> LOCATION: (10)..(10)
<223> OTHER INFORMATION: n = a, g, c, or t
<220> FEATURE:
<221> NAME/KEY: misc_feature
<222> LOCATION: (13)..(13)
<223> OTHER INFORMATION: n = a, g, c, or t

<400> SEQUENCE: 36
sttgntastn ctntgc                                                         16

<210> SEQ ID NO 37
<211> LENGTH: 22
<212> TYPE: DNA
<213> ORGANISM: Artificial Sequence
<220> FEATURE:
```

```
<223> OTHER INFORMATION: primer

<400> SEQUENCE: 37
acgttgtaaa acgacggcca gt                                              22

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
gtaatacgac tcactatagg gcga                                            24

<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
gagtcgacct gcaggcatgc a                                               21

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
cttccggctc gtatgttgtg tgg                                             23

<210> SEQ ID NO 41
<211> LENGTH: 25
<212> TYPE: DNA
<213> ORGANISM: Artificial Sequence
<220> FEATURE:
<223> OTHER INFORMATION: primer

<400> SEQUENCE: 41
gagcggataa caatttcaca cagga                                           25

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
ttaggtgaga ctatagaata ctca                                            24

<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
taacaacatg agaattacta atccg                                           25
```

```
<210> SEQ ID NO 44
<211> LENGTH: 23
<212> TYPE: DNA
<213> ORGANISM: Artificial Sequence
<220> FEATURE:
<223> OTHER INFORMATION: primer

<400> SEQUENCE: 44
catgtatcca agttcgtagc tag                                              23

<210> SEQ ID NO 45
<211> LENGTH: 26
<212> TYPE: DNA
<213> ORGANISM: Artificial Sequence
<220> FEATURE:
<223> OTHER INFORMATION: primer

<400> SEQUENCE: 45 ttggttttttt tgaatgaagg gtatat                                          26

<210> SEQ ID NO 46
<211> LENGTH: 24
<212> TYPE: DNA
<213> ORGANISM: Artificial Sequence
<220> FEATURE:
<223> OTHER INFORMATION: primer

<400> SEQUENCE: 46
aattcatgcc cacaagtaca gtac                                             24

<210> SEQ ID NO 47
<211> LENGTH: 24
<212> TYPE: DNA
<213> ORGANISM: Artificial Sequence
<220> FEATURE:
<223> OTHER INFORMATION: primer

<400> SEQUENCE: 47
ctgaaacaca ggaaaaatcc cgtt                                             24

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
tgcataggcc ctgtttagtt ctaa                                             24

<210> SEQ ID NO 49
<211> LENGTH: 1552
<212> TYPE: DNA
<213> ORGANISM: Oryza sativa
<220> FEATURE:
<221> NAME/KEY: Xa31 promoter of IRBB31 allele (resistant allele)
<222> LOCATION: (1)..(1552)
<223> OTHER INFORMATION:
<220> FEATURE:
<221> NAME/KEY: Xa31 promoter of IRBB31 allele (resistant allele)
<222> LOCATION: (1)..(1552)
<223> OTHER INFORMATION:

<400> SEQUENCE: 49
gctgaaccaa acagttttag ctccatcgaa gaaaggagtt atactgattg gaatgctctc      60
acagtaaaaa aaacaaggaa gtagagctgg attttagaca gttctacaag aagttagaac     120
```

-continued

```
tctaccaaaa ttggaattttt ggatgatggt cttttaaaaa ctcgattgca ggaataaaat      180
tttacggctt gaaacttaca aaatgattag aaaagataac atgcctcagc gatttgtaaa      240
aaagtgaaca aataaaaatc tacaatacca ctaaactatt gctttatttt ggggacattg      300
cttaccattg aaaaacaac taaccgtaaa tacgaacacc catatcaaat atactatcac       360
tgataaaata atcaattgta aattcaagca cacatattag tatagtactt taactcgatt      420
ggatagaaga aacctaacta atttaagcta tgcctcacaa caaaaggta taaatttttt      480 aaggcttctt ttttttttctt gcgtttgcta gtttatgctt ttaagatgtt tatacctttt    540
actcccctca ttcactgttt aaatacaatg ggaattagtg aaatcaatga gagttcaaac     600
ttcgaaacac tgaatacatg ttattttgga ttgaaatcaa atcgaatcag tcaaattcaa     660
ataggaggag aacataggc attcttcctt cttcagcgg gcaccattga attcagatac       720
tgcttcgcct agtctctgtc caagactcca catttctga tggtgatggg gaactctgaa      780
actataggag gaagaataaa atgaagaatg cagaaatgaa tagtaatttg tgttttttaa     840
ttcttcttca attccacctt aggatccaac ttcagtccaa atccaaagta atgcaactgc     900
cactagatca ggctagagct tcaaattcaa ctccaaaaac ctccgtaaag tggcacacac    960
agaggaaaaa tcctggattc gtcactgccc atcaacatct gctttcgcct cccaattcct    1020
gctttctgaa atctgctttc gccgaattca tgccttcttg aattatgctt tcttagaccc   1080
tctttagatg ggactaaaac ttttactctc tatcacatcg gatgtttgga cactaattat   1140
aaatattaaa cgtagactat taataaaacc catctataat cttgtattaa ttcgcgagac   1200
gaatctattg agcctaatta atccatgatt agcctatgtg atgctataat aaacattctc   1260
taattataaa ttaattgggc ttaaaaaatt tgtctcgcgt attagctttc atttatataa    1320
ttagttttat aaatagtcta tatttaatac tctaaattag tgtctaaata cagggactaa    1380
agttaagtca ctggatccaa acaccaccta aggttttctt gtgtacttgt gaattgtggt    1440
tgactacgac tactagtgct ataaatagaa gaagagaccc atagagagca tcagagcaaa   1500
gtactcctaa aagacagcca cacacactga gacacccaag aagctgcctc ca            1552
```

<210> SEQ ID NO 50
<211> LENGTH: 541
<212> TYPE: DNA
<213> ORGANISM: Oryza sativa
<220> FEATURE:
<221> NAME/KEY: Xa31 3' regulation region of IRB31 allele
    (resistant allele)
<222> LOCATION: (1)..(541)
<223> OTHER INFORMATION:

<400> SEQUENCE: 50

```
ttctcctccg tgtccggtgg tcatcttctt ctccgtgctt ttgctctgga gttgagtacg      60
gatctgtgtg tactgcattc ttgcttaatt agtgccctac acgttatgct ttcgaaacat    120 catcttttt cagtatagtt caataaattt cagctcaaat ttgtcctcca agacgagttc     180
tccatccaaa cgaaacttat ggtgttccgt tgtttgggcc gatttatat gttggaaatg     240 tacagacttc atagtactgt gtttctttt tggaataagt tcaccagagg ttccttaact    300
taacggcgat atttttttag gtcctttaac cacaaaacca gaaatgtgca ccctaaact    360 ttcacaatcc gtgcacaaga ggtcctatgg cagtatacgt gggtggtttc gctgacgtga   420
catcctagtc agcaaaaata aataaataag taagtgggc ccatatgtaa gtgagagaaa     480
acgatgcggg ccccacatcc cttctttttc cccctttctt ctcctctcgt cttcttcgac   540
``` g                                                                          541

<210> SEQ ID NO 51
<211> LENGTH: 1583
<212> TYPE: DNA
<213> ORGANISM: Oryza sativa
<220> FEATURE:
<221> NAME/KEY: xa31 promoter of IR24 allele (susceptible allele)
<222> LOCATION: (1)..(1583)
<223> OTHER INFORMATION:

<400> SEQUENCE: 51

```
gctgaaccaa acagttttag ctccatcgaa gaaggagtt atactgattg gaatgctcac        60
agttaaaaaa aacaaggaag tagagctgga ttttagacag ttctataaga agttagaact       120
ctaccaaacg gatagttaat tggaattttg gatgatggtc ttttaaaaac tcgattgcag       180
gaataaaatt ttacggcttg aaacttacaa aatgattaga aaagataaca tgcctcagcg       240
atttgtaaaa aagtgaacaa ataaaaatct acaataccac taaactattg ctttatttg        300
gggacattgc ttaccattga aaaacaact aaccgtaaat acgaacaccc atgtcaaata        360
tactatcact gataaaataa tcaattgtaa attcaagcac acatattagt atagtacttt       420
aactcgattg gatagaagaa acctaactaa tttaagctat gcctcacaac aaaaaggtat       480
aaattttta aggcttcttt tttttcttg cgtttgctag tttatgcttt taagatgttt         540
atactttta ctcccctcat tcactgttta aatacaatgg gaattagtga aatcaatgag        600
agttcaaact tcgaaacact gaatacatgt tattttggat tgaaatcaaa tcgaatcagt      660
caaattcaaa taggaggagg aacataggca ttcttccttt cttcagcggg caccattgaa      720
ttcagatact gcttcgccta gtctctgtcc aagactccac attttctgat ggtgatgggg     780
aactctgaaa ctataggagg aagaataaaa tgaagaatgc agaaatgaat agtaatttgt     840
gttttttaat tcttcttcaa ttccaccta ggatccaact tcagtccaaa tccaaagtaa      900
tgcaactgcc actagatcag gctagagctt caaattcaac tccaaaaacc tccgtaaagt    960
ggcacacaca gaggaaaaat cctggattcg tcactgccca tcaacatctg ctttcgcctc   1020
ccaattcctg ctttctgaaa tctgctttcg ccgaattcat gccttcttga attatgcttt   1080
cttagacccct ctttagatga gactaaaact tttactctct atcacatcgg atgtttggac   1140
actaattata aatattaaac gtagactatt aataaaaccc atctataatc ttgtattaat   1200
tcgcgtgacg aatctattga gcctaattaa tccatgatta gcctatgtga tgctataata   1260
aacattctct aattataaat taattgggct taaaaatttt gtctcgcgta ttagctttca   1320
tttatgtaat tagttttata aatagtctat atttaatact ctaaattagt gtctaaatac   1380
agggactaaa gttaagtccc tggatccaaa cgccacctaa ggttttcttg tgtacttgtg   1440
aattgtggtt tcttgtgtac ttgtgaattg tggttgacta cgactacgag tgctataaat   1500
agaagagacc aatagagagc atcagagcaa agtactccta aaagacagcc acacacactg   1560
agacacccaa gaagctgcct cca                                           1583
```

<210> SEQ ID NO 52
<211> LENGTH: 541
<212> TYPE: DNA
<213> ORGANISM: Oryza sativa
<220> FEATURE:
<221> NAME/KEY: xa31 3' regulation region of IR24 allele
       (susceptible allele)
<222> LOCATION: (1)..(541)
<223> OTHER INFORMATION:

-continued

```
<400> SEQUENCE: 52
ttctcctccg tgtccggtgg tcatcttctt ctccgtgctt ttgctctgga gttgagtacg        60
gatctgtgtg tactgcattc ttgcttaatt agtgccctac acgttatgct ttcgaaacat       120 catcttttt  cagtatagtt caataaattt cagctcaaat ttgtcctcca agacgagttc       180
tccatccaaa cgaaacttat ggtgttccgt tgtttgggcc gattttatat gttggaaatg       240
tacagacttc atagtactgt gtttcttttt tggaataagt tcaccagagg ttccttaact       300
taacggcgat attttttag  gtcctttaac cacaaaacca gaaatgtgca cccctaaact       360
ttcacaatcc gtgcacaaga ggtcctatgg cagtatacgt gggtggtttc gctgacgtga       420
catcctagtc agcaaaaata aataaataag taagtggggc ccatatgtaa gtgagagaaa       480
acgatgcggg ccccacatcc cttctttttc cccctttctt ctcctctcgt cttcttcgac       540
g                                                                      541
```

NUCLEIC ACIDS FROM RICE CONFERRING RESISTANCE TO BACTERIAL BLIGHT DISEASE CAUSED BY *XANTHOMONAS* SPP

CROSS REFERENCE TO RELATED APPLICATION

This application is a 35 U.S.C. § 371 National Phase Entry Application from PCT/SG2003/000191, filed Aug. 13, 2003, designating the United States.

FIELD OF THE INVENTION

The present invention relates generally to plant molecular biology and genetics and to nucleic acids and methods for conferring resistance to bacterial disease in plants.

The publications and other materials used herein to illuminate the background of the invention or provide additional details respecting the practice are incorporated by reference and for ease of reference are included in the Bibliography.

BACKGROUND OF THE INVENTION

One of the important plant defense mechanisms that has evolved during the co-evolution of the plant-pathogen interaction is the so-called gene-for-gene interaction model (Flor, 1971). According to a simple formation of this model, plant resistance (R) genes encode specific receptors for molecular signals generated by avirulence (Avr) genes from a pathogen Subsequent signal transduction pathway(s) then carry the signal to a set of downstream target genes that initiate the host defenses Dangl, 2001) The R gene-mediated defenses typically involve a rapid, localized necrosis, or hypersensitive response (HR) at the site of infection and the localized formation of antimicrobial chemicals and proteins that restrict growth of the pathogen (Greenberg, 1997).

Numerous R genes have been cloned and characterized from dicots (Hulbert et al., 2001). However, only several R genes have been cloned from the cereals that contribute heavily to the supply of food for humans and feed for livestock, in part because of the complex genomes of most of these crop plants. In rice (*Oryza sativa*), the first cloned R gene was the Xa21 bacterial blight R gene that encodes a protein with putative extracellular receptor and cytoplasmic kinase domains (Song et al. 1995; U.S. Pat. No. 5,859,339). Three other rice R genes, the Xa1 bacterial blight R gene (Yoshmura et al., 1998) and two rice blast R genes, Pi-b (Wang et al., 1999) and Pi-ta (Bryan et al., 2000; U.S. Pat. No. 6,479,731 B1) encode putative cytoplasmic receptor proteins with a nucleotide binding site. Pita protein also shows specifically physical interaction with AVR-Pi-ta protein both in the yeast two-hybrid system and an in vitro binding assay (Jia et al., 2000).

Bacterial blight (BB) disease caused by *Xanthomonas* species affects virtually all crop plants and leads to extensive crop losses worldwide. BB in rice, caused by *Xanthomonas oryzae* pv *oryzae* (Xoo) has been one of the most serious disease in rice, affecting production in irrigated and rain-ed lowland ecosystems throughout Asia, northern Australia, mainland Africa, the southern part of United States and Latin America. Yield loss due to the disease ranges from 20 to 30% (Ou 1985). To date, the best control for BB in rice has been the use of varietal resistance. More than 20 R genes against BB have been identified (Kinoshita 1995; Lin et al., 1996; Zhang et al., 1998; Khush et al., 1999; Gao et al., 2001) and two, Xa21 and Xa1, have been cloned. Xa21 originates from the wild species *Oryza longistaminata* and confers resistance to multiple Xoo isolates in transgenic plants (Wang et al., 1996) while Xa1 confers a high level of race-specific resistance to race 1 strains of Xoo in Japan (Yoshmura et al., 1998).

A novel BB-resistant locus was identified from a BC2 plant (plant 78-1) of a cross between cultivated rice *O. sativa* cv IR3191745-3-2 (I3 1917) and wild rice species *Oryza minuta* Acc. 101141 (Amante-Bordeos et al., 1992). This report also suggested that a single gene or closely linked genes conferred race-specific resistance to Xoo stain PXO99 (race 6) of the BB pathogen from the Philippines.

SUMMARY OF THE INVENTION

In one embodiment, the present invention provides the cloning and characterization of a gene encoding the resistance gene Xa31, which confers resistance to bacterial blight disease. In a preferred embodiment, the resistance is to bacterial blight disease caused by *Xanthomonas* species.

In another embodiment, the invention provides a composition of matter which comprises a nucleic acid according to SEQ ID NO: 1, wherein the sequence confers resistance to bacterial blight to a plant transfected with the nucleic acids. In other embodiments, the invention provides a substantially homologous variant of SEQ ID NO:1 or a nucleic acid which hybridizes under stringent conditions to said sequence and confers resistance to bacterial blight to a plant transfected with the nucleic acid. In another embodiment, the invention provides a nucleic acid that comprises at least 100 contiguous base pains of SEQ ID NO:1 and which confers resistance to bacterial blight to a plant transfected with the nucleic acid.

In another embodiment the invention provides a method of making a plant resistant to bacterial blight, the method comprising transfecting the nucleic acid of SEQ ID NO:1 into said plant or transfecting said nucleic acid into a plant cell or cells and growing a plant from said cell or cells wherein said nucleic acid confers resistance to bacterial blight when transfected into a plant that is not resistant to bacterial blight. In another embodiment, the method of making a plant resistant to bacterial blight comprises transfecting a nucleic acid fragment of at least 100 base pairs of SEQ ID NO:1 into said plant wherein said fragment confers resistance to bacterial blight when transfected into a plant that is not resistant to bacterial blight.

In another embodiment the invention provides a composition of matter which comprises one or more nucleic acids selected from the group consisting of SEQ ID NO:2, SEQ ID NO:3, SEQ ID NO:4, SEQ ID NO:49, SEQ ID NO-50, SEQ ID NO:51 and SEQ ID NO:52, wherein said one or more nucleic acids confers resistance to bacterial blight when transfected into a plant that is not resistant to bacterial blight. In other embodiments, the invention provides one or more substantially homologous variants of said nucleic acids.

In another embodiment, the invention provides a method of making a plant resistant to bacterial blight, the method comprising transfecting at least one nucleic acid selected from the group consisting of SEQ ID NO:2, SEQ ID NO:3, SEQ ID NO:4, SEQ ID NO:49 SEQ ID NO;50, SEQ ID NO:51 and SEQ ID NO;52 into said plant or into a plant cell that is not resistant to bacterial blight and growing a plant there from.

In another embodiment, the invention provides a method of making a plant resistant to bacterial blight, the method comprising transfecting the plant with a fragment of at least 100 contiguous base pairs of SEQ ID NO:1 which confers resistance to bacterial blight to a plant that is not resistant to bacterial blight. In another embodiment, the invention provides a method of making a plant resistant to bacterial blight, the method comprising transfecting a plant cell with a fragment of at least 100 contiguous base pairs of SEQ ID NO:1 which confers resistance to bacterial blight disease and growing a plant from the plant cell.

In yet a further embodiment the invention provides a composition of matter which comprises an isolated nucleic acid encoding a polypeptide as in SEQ ID NO:5 or a fragment thereof or a substantially homologous variant thereof of said isolated nucleic acid.

In another embodiment the invention provides a method of making a plant resistant to bacterial blight, the method comprising expressing in said plant a nucleic acid encoding SEQ ID NO:5.

In other embodiments, the invention provides methods of making plants resistant to bacterial blight which comprise transfecting one or more nucleic acids of the invention into a plant cell and growing a plant from the cell.

In other embodiments, the invention provides vectors, which in a preferred embodiment are expression vectors, cells, which in a preferred embodiment are plant cells and/or plants, any of which may comprise a nucleic acid of the present invention. In other embodiments, the vectors, cells and plants may comprise fragments or substantially homologous sequences which will hybridize to said sequences under stringent conditions and confer resistance to bacterial blight when transfected to a plant that is not resistant.

In another embodiment, the invention provides a transgenic plant, wherein the plant is transfected with the nucleic acid of SEQ ID NO:1 and wherein the plant is resistant to bacterial blight.

In another embodiment, the invention provides a transgenic plant, wherein the plant is transfected with a nucleic acid encoding polypeptide of SEQ ID NO:5, wherein said polypeptide is expressed in said plant In another embodiment, the invention provides a cell transformed with a nucleic acid encoding said polypeptide wherein said polypeptide is expressed in said cell.

In another embodiment the invention provides a method of making a plant resistant to bacterial blight which comprises transfecting the plant with a nucleic acid comprising one or more regulatory regions of SEQ ID NO:1. In one embodiment, the invention provides a method of making a plant resistant to bacterial blight which comprises transfecting the plant with a nucleic acid comprising one or more of SEQ ID NO:49, SEQ ID NO:50, SEQ ID NO:51 and SEQ ID NO:52. In another embodiment the invention provides a method of making a plant resistant to bacterial blight which comprises transfecting the plant with a nucleic acid selected from the group consisting of SEQ ID NO:49, SEQ ID NO:50, SEQ ID NO:51 and SEQ ID NO:52 operably linked to a heterologous gene.

BRIEF DESCRIPTION OF THE FIGURES

FIG. 9 shows the comparison of the promoters at TATA box regions of resistant (IBB31) (SEQ ID NO:53) and susceptible (IR24) (SEQ ID NO:54) alleles of the Xa31 gene

DETAILED DESCRIPTION OF THE PREFERRED EMBODIMENTS OF THE INVENTION

Figure 1:
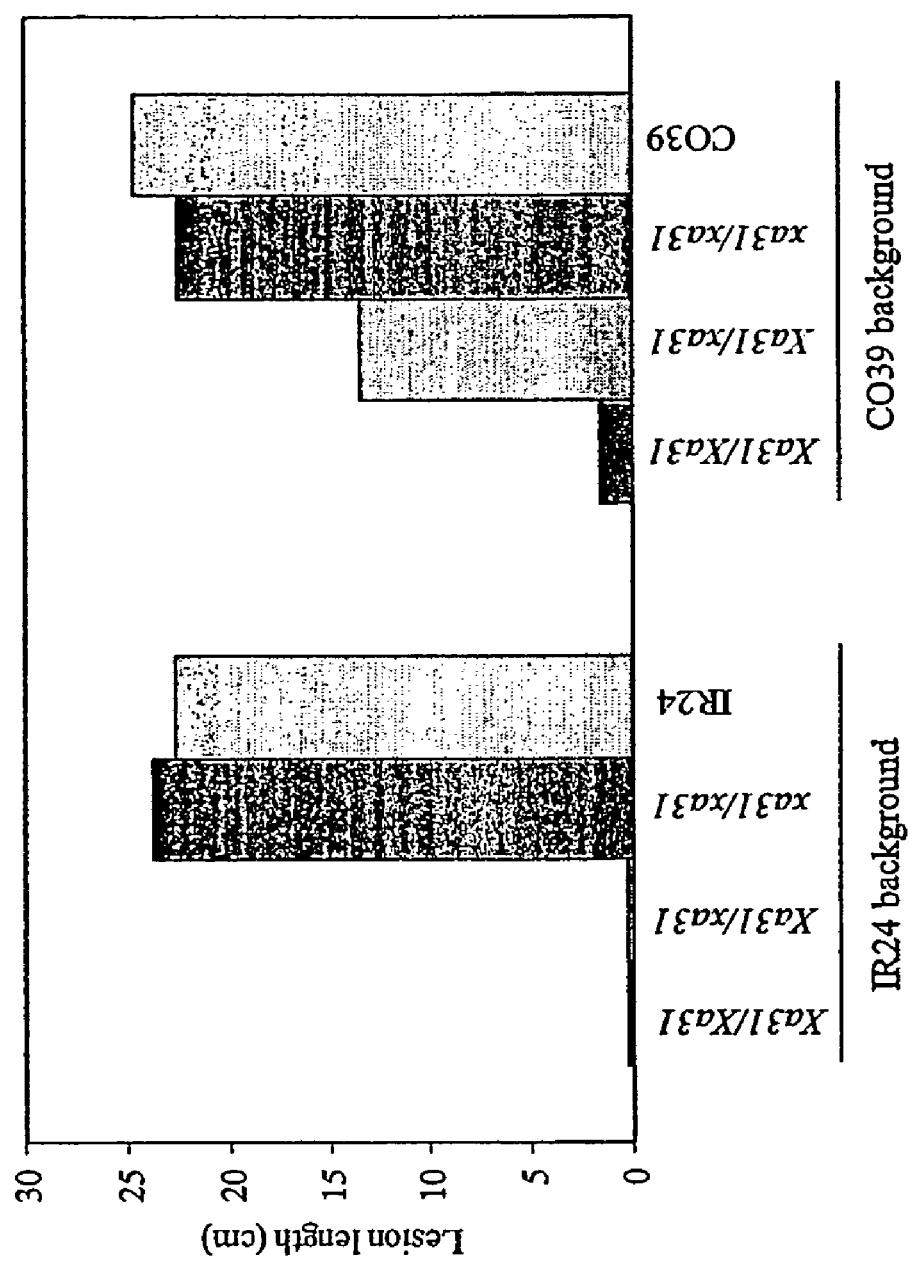
FIG. 1 shows the reactions of Xa31 to *Xanthomonas oryzae* pv. *orzyae* strain PXO99 in different genetic background.

In one embodiment, the invention provides isolated nucleic acids which encode a polypeptide of SEQ ID NO:5. In another embodiment the invention provides an isolated nucleic acid selected from the group consisting of SEQ ID NO:1, SEQ ID NO;2, SEQ ID NO:3, SEQ ID NO:4, SEQ ID NO:49, SEQ ID NO:50, SEQ ID NO:51 and SEQ ID NO:52. In another embodiment, the invention provides a transgenic plant or plant cell transformed with one or more nucleic acids of the invention, wherein the presence of the nucleic acid in the cell provides resistance to bacterial blight disease to the plant or cell. The present disclosure demonstrates that transfection of a plant (or transfecting a plant cell and growing a plant therefrom) with a nucleic acid as in SEQ ID NO:1 results in a plant that is resistant to bacterial blight. These results also demonstrate that some combination of one or more nucleic acids selected from the group consisting of SEQ ID NO:2, SEQ ID NO:3, SEQ ID NO:4, SEQ ID NO:49, SEQ ID NO:50, SEQ ID NO:51 and SEQ ID NO:52, and nucleic acids encoding SEQ ID NO:5 are responsible for conferring a plant with resistance to bacterial blight. In another embodiment, the invention provides an isolated nucleic acid that regulates expression of the phenotype of bacterial blight resistance, wherein the nucleic acid comprises one or more of SEQ ID NO:49, SEQ ID NO50, SEQ ID NO:51 and SEQ ID NO:52 and wherein the nucleic acid may optionally be operably linked to a nucleic acid encoding a heterologous polypeptide. In another embodiment, the invention provides an expression vector wherein said vector comprises a nucleic acid encoding a polypeptide as described herein. Heterologous proteins or peptides can include proteins of R genes or proteins of defense genes from rice or other plants as known to those of ordinary skill in the art. Non-limiting examples can include rice bacterial blight R proteins Xa1, Xa2 or defense proteins such as, e.g., PR1 firm rice.

Once a nucleic acid has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable transformation include leaf tissues, root tissues, meristems, protoplasts, hypocotyls, cotyledons, scutellum, shoot apex, root, immature embryo, pollen, and anther. Some non-limiting examples of methods that can be employed in transforming plants and plant cells are provided below.

A polynucleotide or nucleic acid is said to "encode" a polypeptide if, in its native state or when manipulated by methods well known to those skilled in the art it can be transcribed and/or translated to produce the mRNA for and/or the polypeptide ox a fragment thereof.

An "isolated" or "substantially pure" nucleic acid (e.g., an RNA, DNA or a mixed polymer) or polypeptide is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems. The present invention contemplates nucleic acids which comprise isolated Xa31 nucleic acids.

The polynucleotide compositions of this invention include RNA, cDNA, genomic DNA, synthetic forms, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included arc synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. The polynucleotides of the invention may be isolated or substantially pure.

The present invention provides recombinant nucleic acids comprising the Xa31 gene. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the described sequences may be employed, it will often be altered, e.g., by deletion, substitution or insertion.

"Protein modifications or fragments" are provided by the present invention for wildtype and mutant Xa31 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by persons of ordinary skill in the art. A variety of methods for labeling polypeptides and of substituents or labels useful for such purposes are well known by persons of ordinary skill in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation.

Besides substantially full-length proteins, the present invention provides for biologically active fragments of the polypeptides. Significant biological activities include ligand-binding, immunological activity and other biological activities characteristic of proteins. The term "polypeptide" as used herein refers to both a full length protein and a portion of the protein as a polypeptide fragment.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The present invention also provides for fusion polypeptides, comprising Xa31 polypeptides and fragments thereof and polypeptides or fragments of other proteins as known in the art Homologous polypeptides may be fusions between two or more polypeptide sequences or between the sequences of Xa31 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding and may include for example partners such as immunoglobulins, bacterial β-galactosidase, trpE, protein A, β-lactamase, alpha amylase, alcohol dehydrogenase and yeast alpha mating factor.

Fusion proteins will typically be made by either recombinant nucleic acid methods, as described below, or may be chemically synthesized. Techniques for the synthesis of polypeptides are well known by persons of ordinary skill in the art.

Other protein modifications include amino acid substitution. Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known to persons of ordinary skill in the art and typically include, though not exclusively, substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with a polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art. Alternatively, the substitution of like amino acids can be made effectively on the basis of hydrophilicity. The importance of hydrophilicity in conferring interactive biological function of a protein is generally understood in the art (See e.g. U.S. Pat. No. 4,554,101). The use of the hydrophobic index or hydrophilicity in designing polypeptides is further discussed in U.S. Pat. No. 5,691,199.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. This phrase is also meant to encompass a gene which is removed from its normal regulatory expression constraints, as in the case where a gene product is overexpressed due to the presence of multiple copies of the gene or up regulated promoter or enhancer signals, increased mRNA or protein half life and the like.

"Regulatory sequences" refers to those sequences which affect the expression of the gene (including transcription of the gene, and translation, splicing, stability or the like of the messenger RNA).

Large amounts of the polynucleotides of the present invention may be produced by a suitable host cell transformed with a nucleotide sequence encoding mutant or wildtype Xa31 protein. Natural or synthetic polynucleotide fragments coding for the peptide or a desired fragment can be incorporated into recombinant polynucleotide constructs (vectors), usually DNA constructs, capable of introduction into and replication in a prokaryotic or eukaryotic cell. Usually the vectors will be suitable for replication in a unicellular host, such as yeast or bacteria, but may also be intended for introduction to (with and without integration within the genome) cultured mammalian or plant or other eukaryotic cell lines. The most commonly used prokaryotic hosts are strains of Escherichia coli, although other prokaryotes, such as Bacillus subtilis or Pseudomonas may also be used. Mammalian or other eukaryotic host cells, such as those of yeast, filamentous fungi, plant insect, or amphibian or avian species, may also be useful for production of the proteins of the present invention. As is well known in the relevant art regulating polynucleotide expression can result in regulation of polypeptides encoded by the polynucleotide.

Antibodies that specifically bind the polypeptides of the present invention are also contemplated. Using techniques well known to a person of ordinary skill in the art, the polypeptides can be used as antigen for inducing an antibody response in an animal and the antibodies generated can be screened for antibodies with specificity for a polypeptide of the present invention. The present invention also provides polyclonal and/or monoclonal antibodies and fragments thereof, and immunologic binding equivalents thereof, which are capable of specifically binding to the Xa31 polypeptides and fragments thereof or to polynucleotide sequences from the Xa31 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the Xa31 polypeptide or fragment Monoclonal antibodies may be made by injecting mice with the protein polypeptides, fusion proteins or fragments thereof. Monoclonal antibodies will be screened by ELISA and tested for specific immunoreactivity with Xa31 polypeptide. Antibodies can also comprise single chain or multimer recombinant antibodies or fragments thereof.

Vectors will include an appropriate promoter and other necessary vector sequences that are functional in the selected host. There may include, when appropriate, those naturally associated with the Xa31 nucleic acid and protein expression and may include alternative or additional regulatory sequences operably linked to the recombinant Xa31 gene in order to control Xa31 gene expression, as well known in the art. Many useful vectors are known in the art and may be obtained from such vendors as Stratagene, New England BioLabs, Promega Biotech, and others. Promoters such as the trp, lac and phase promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. "Operably linked" refers to a juxtaposition wherein the components so described are in a relationship permitting them to function in their intended manner. For instance, a promoter is operably linked to a coding sequence if the promoter affects its transcription or expression.

Expression and cloning vectors preferably contain a selectable marker gene. Typical marker genes encode proteins that a) confer resistance to antibiotics or other toxic substances, e.g. ampicillin, neomycin, methotrexate, etc.; b) complement auxotrophic. deficiencies, or c) supply critical nutrients not available from complex media, e.g. the gene encoding D-alanine racemase for Bacilli. The choice of an appropriate proper selectable marker will depend on the host cell, and appropriate markers for different hosts are well known to persons of ordinary skill in the art.

The vectors containing the nucleic acids of interest can be transcribed in vitro, and the resulting RNA introduced into the host cell by well-known methods, e.g., by injection, or the vectors can be introduced directly into host cells by methods well known to persons of ordinary skill in the art, which vary depending on the type of cellular host, including electroporation; transfection employing calcium chloride, rubidium chloride, calcium phosphate, DEAE-dextran, or other substances; microprojectile bombardment, lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Clones are selected by using markers, depending on the mode of the vector construction. The, marker may be on the same or a different DNA molecule, preferably the same DNA molecule In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention are useful not only for the production of the nucleic acids and polypeptides of the present invention, but also, for example, in studying the characteristics of Xa31 polypeptides. Plant cells transformed with the polynucleotides of the present invention are useful also for growing plants expressing the polynucleotides and polypeptides of the present invention. The nucleotides of the present invention can also be transformed into plants that have already undergone some growth.

Plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal. A plant promoter fragment can be employed which will direct expression of Xa31 in all tissues of a generated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, and the GRP1-8 promoter.

Alternatively, the plant promoter can direct expression of a polynucleotide of the present invention in a specific tissue or may be otherwise under more precise environmental or developmental control. Such promoters are referred to here as "inducible" promoters Environmental conditions that may effect transcription by inducible promoters include pathogen attack, anaerobic conditions, or the presence of light. Examples of inducible promoters are the Adhl promoter, which is inducible by hypoxia or cold stress, the Hsp70 promoter, winch is inducible by beat stress, and the PPDK promoter, which is inducible by right.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the Xa31 gene. These promoters can also be used, for example, in recombinant expression cassettes to drive expression of antisense nucleic acids to reduce, increase, or alter concentration and/or composition of the Xa31 protein in a desired tissue. Thus, in some embodiments, the nucleic acid construct will comprise a promoter functional in a plant cell, such as in *Zea mays* or tobacco, operably linked to Xa31, Promoters useful in these embodiments include the endogenous promoters driving expression of Xa31.

Similar to the electroporation method is a method in which the desired gene and protoplasts are mixed and the mixture is treated with polyethylene glycol ("PEG"), thereby introducing the gene into the protoplasts. This method is different from the electroporation method in that PEG is used instead of an electric pulse (Zhang W. et al., 1988, Datta et al., 1990 and Christou et al., 1991).

Other methods include 1) culturing seeds or embryos with nucleic acids (Topfer R. et al., 1989, Ledoux et al., 1974) 2) treatment of pollen tube, (Luo et al., 1988) 3) liposome method (Caboche, 1990) and 4) the microinjection method (Neuhaus G. et at, 1987).

Known methods for regenerating plants from transformed plant cells may be used in preparing transgenic plants of the present invention. Generally, explants, callus tissues or suspension cultures can be exposed to the appropriate chemical environment (e.g. cytokinin and auxin) so the newly grown cells can differentiate and give rise to embryos which then regenerate into roots and shoots.

The invention is further illustrated by the following examples, which are not intended to be limiting.

EXAMPLES

Example 1

Disease Resistance Gene Xa31 Conferring Adult resistance to Multiple Xoo Strains Since the $BC_2$ progeny containing the Xa31 gene was the interspecific hybrids of *O. sativa* cv IR3191745-3-2 and *O. minuta* Acc. 101141 (Amante-Bordeos et al. 1992), repeated backcrossing was used to remove the undesirable traits from wild rice. A highly resistant plant with less undesirable agronomic traits was selected from the cross between 78-1-5BC2F3 #169 and IR24 as pollen donor to cross with susceptible cultivar CO39 at University of California at Davis (unpublished result). Probably due to other genetic factors present in CO39 or other two cultivars (IR3 1917-45-3-2 and IR24) used in the previous backcrosses that interfere with Xa31, there was a great variation in disease resistance in the progeny from the cross. To simplify the genetic background of the Xa31 germplasm, we selected a resistant F3 plant from the progeny as male to backcross with concurrent susceptible cultivars IR24 and CO39, respectively. Briefly, ten generations of backcrosses were carried out to transfer Xa31 into IR24 genetic background and one of the $BC_{10}F_3$ plants was designated as IRBB31 for Xa31 near-isogenic line. In the meantime, seven generations of backcrosses were made to transfer Xa31 into CO39 genetic background. For genetic mapping of Xa31 locus, 863 resistant plants (Xa31 Xa31) of backcross lines, 1245 susceptible plants (Xa31 Xa31) and 261 resistant plants (Xa31 Xa31 or Xa31 Xa31) from segregating populations were used for genetic linkage analysis. A total of 3875 gametes were analyzed in this mapping population.

To monitor the presence of the Xa31 gene in the backcross plants and to confirm the inheritance of Xa31 as single dominant locus, we evaluated disease reaction for plants across various generations with Xoo strain PXO99. In one experiment with BC2F1 plants of IR24 genetic background, 208 resistant plants aid 253 susceptible plants were detected, respectively (1:1 segregation with $\chi^3=0.019$, p>0.80, n=1). In another experiment with BC10F2 plants of IR24 genetic background, 232 resistant plants were observed and 47 susceptible plants were scored (3:1 segregation with $\chi^2=0.118$, 0.5<P<0.80, n=1). In the later experiment, we detected the genotype of all plants with two closely linked flanking markers. There was no difference in lesion length between homozygote (Xa31Xa31) and heterozygote (Xa31xa31) of the resistant plants and the mean lesion length of the resistant plants (Xa31xa31 or Xa31xa31) was only 0.3±0.2 cm, while that of the susceptible plants (xa31xa31) was 23.8±5.8 cm (FIG. 1). The results of these two experiments strongly suggest that resistance is controlled by a single dominant locus, which is consistent with the previous study (Amante-Bordeos et al. 1992). In order to check whether Xa3l shows similar genetic performance in CO39 genetic background, thirty-eight $BC_7F_2$ plants from a 13C7 backcross with CO39 were inoculated with PXO99. Three Xa3l homozygous plants (Xa3lXa3l) were resistant (lesion length=1.6±1.4 cm) while 12 recessive homozygotes (Xa3lax3l) were susceptible to PXO99 (lesion length=22.6±5.8 cm) (FIG. 1). However, 23 heterozygotes (Xa3lxa3l) showed great deviation in disease phenotype from moderately resistant (3.0 cm<lesion length≦6.0 cm) and moderately susceptible (6.0 cm<lesion length≦9.0 cm) to fully susceptible (lesion length>9.0 cm). The mean lesion length of these plants was 13.5±7.0 cm (FIG. 1). Even though the mean lesion length of the heterozygotes showed they were susceptible to PXO99, we still can make a general conclusion by comparing the mean lesion length of the plants with different genotypes, that Xa3l confers semi-dominant resistance or shows dosage effect for resistance in CO39 genetic background. The inheritance of Xa3l as a semi-dominant R gene was also observed in the genetic background of five parent lines of Chinese hybrid rice when Xa3l was used for marker-assisted breeding program. These results suggest that the expression of Xa3l could be affected by other genetic factors in some genetic backgrounds when plants are heterozygous at the resistance locus. FIG. 1 shows the reactions of Xa3l to *Xanthomonas oryzae* pv. *oryzae* strain PXO99 in different genetic backgrounds. The genotype of each plant was detected by Xa3l flanking markers M3623 and 3612EST2. Standard deviation (SD) was not shown.

Detection of the resistant spectrum of Xa3l in IR24 genetic background was carried out firstly with homozygous BC2F3 plants (data not shown) and then confirmed with IRBB31 plants by inoculating with 35 Xoo strains collected from 11 countries around the world. IRBB21, the near-isogenic line of Xa2l, was used as a resistant control for disease evaluation in this study (Wang et al. 1996). Table 1 summarizes the lesion length and the phenotype of disease reaction. Briefly, among 35 Xoo strains tested, Xa3l conferred high level of resistance to 27 strains and moderate resistance to 3 strains (HB17, JW89011 and PXO71), and showed susceptibility to 5 strains (1947, C4, ZHE173, K202 and 2). Xa3l and Xa2l share most of the incompatible strains tested. Xa3l conferred resistance to A3842 and moderate resistance to JW89011 while Xa2l shows moderately susceptible or susceptible phenotype to the two strains. Neither Xa3l nor Xa2l could confer resistance to the Africa strain 1947. In most of the incompatible reactions between Xa3l or Xa2l and Xoo pathogens, Xa3l plants had shorter lesions than that of Xa2l plants. The lesions observed in incompatible reactions (R and MR in Table 1) of Xa2l measured in this study were longer than that of previous study (Wang et al. 1996), which may partially be attributed to the higher temperature used for inoculation in this study (see materials and methods). Strains A3842 and Thailand 2 were detected to be incompatible to Xa2l in the previous study (Wang et al. 1996) but were compatible in this study. In most of the incompatible reactions between Xa3l and Xoo strains, brown lesion was observed 34 days after inoculation at the cut area. Brown lesion was much more obvious at the infection sites of those leaves that showed highly resistant phenotype with mean lesion length less than 0.5 cm two weeks after inoculation Browning reaction against pathogens was also observed in the interaction of Xa3 and its incompatible Xoo strains (Kaku and Ogawa, 2000). No browning reaction was observed at early stage of infection in the interactions between Xa2l and its incompatible Xoo stains. The difference in browning reaction between Xa3l and Xa-21 against the bacterium suggests that the resistance mechanism of these two genes may be different at molecular level and/or function through different signal transduction pathways.

Figure 2:
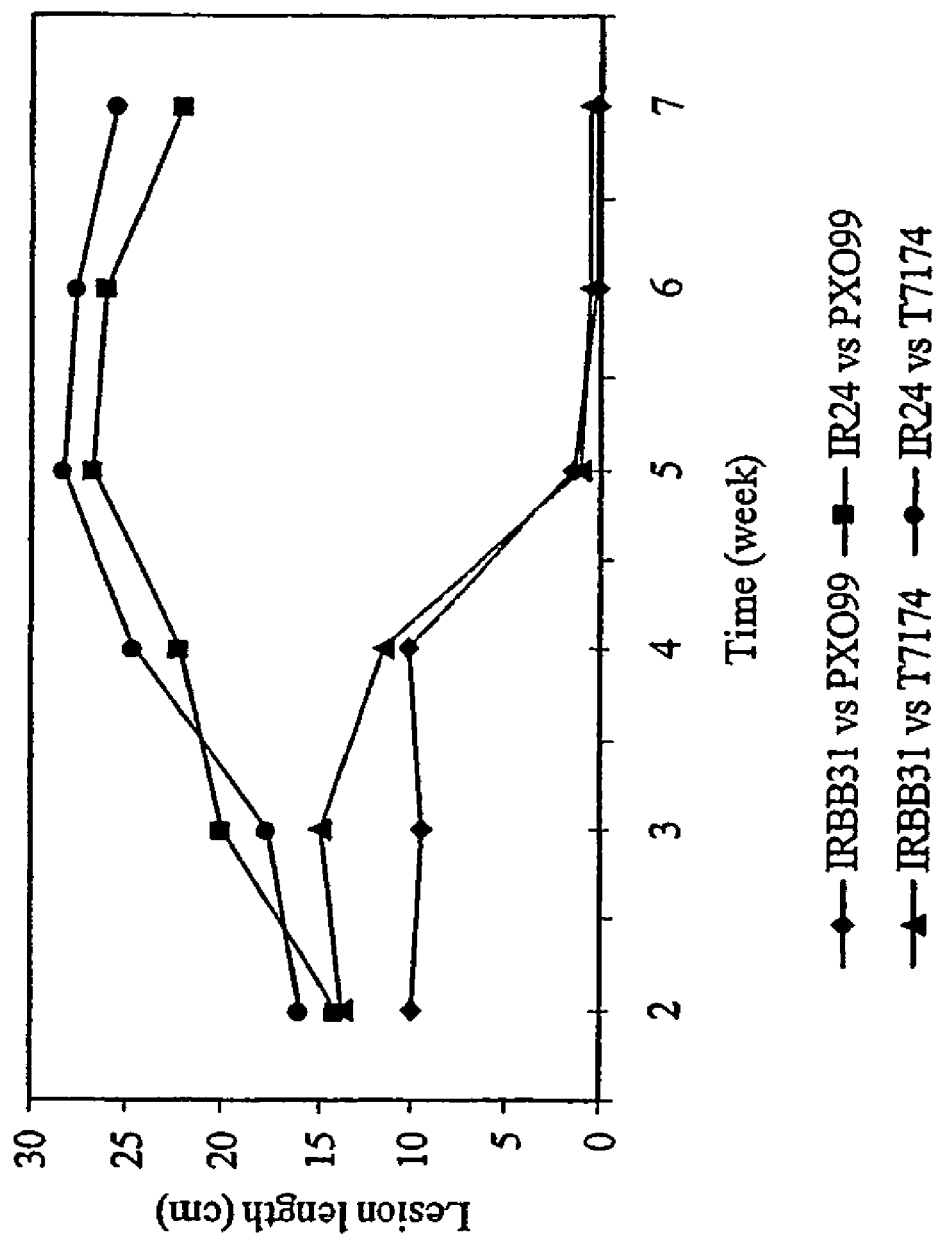
FIG. 2 shows the resistance of Xa31 to *Xanthomonas oryzae* pv. *oryzae* strain PXO99 and T7174 at different developmental stages.

The reaction of Xa3l to bacterial blight at different developmental stages was evaluated with two different Xoo strains, PXO99 and T7174. PXO99 is a representative strain of Philippines race 6 while T7174 is a representative strain of Japanese race 1 (Song et al. 1995; Yoshimura et al. 1998). Both IR24 and IRBB31 were inoculated with bacteria blight pathogens every week starting from two-week-old plants until seven-week-old plants. Only one to two youngest fully expanded leaves of main culm (from seedling stage to active tillering stage) or each tiller (after active tillering stage) were selected for inoculation 1R24 was highly susceptible to the two Xoo strains from seedling stage (before 4-5 weeks) to adult plants (FIG. 2). However, the development of bacterial blight disease was found to be reduced if the pathogens were inoculated on IR24 plants after the booting stage (after 8 weeks, the life cycle of IR24 in Singapore is about 95 days) (data not shown). IRBB31 was also susceptible to the two Xoo strains till 4-week-old even though it had shorter lesions compared to that of IR24. The resistance of IRBB31 to bacterial blight pathogens was drastically increased after 4-week-old and reached almost complete resistance at 5-week-old. Therefore, the resistance conferred by Xa3l could be developmentally regulated and to appears to be activated or induced at the late stage of vegetative growth. Developmental regulation of resistance to bacterial blight was also observed in other studies (Goel and Gupta 1990; Ogawa 1993; Century et al. 1999). Molecular investigation has also demonstrated that expression of Xa2l gene transcript was not correlated with expression of Xa2l disease resistance (Century et al. 1999). FIG. 2 shows the resistance of Xa3l to *Xanthomonas oryzae* pv. *oryzae* strain PXO99 and T7174 at different developmental stages. Lesion length is shown in mean. Standard deviation (SD) is not included. Reactions are indicated.

TABLE 1

Comparison of the resistance spectrum of Xa31 and Xa21 to different Xoo strains in IR24 genetic background[a]

| Strain | Origin | IRBB31 | IRBB21 | IR24 |
| --- | --- | --- | --- | --- |
| 1947 | Africa | 21.5[b] ± 2.2[c] (S[d]) | 18.1 ± 4.4 (S) | 21.2 ± 3.3 (S) |
| Aust-2031 | Australia | 0.3 ± 0.2 (R) | 2.4 ± 0.9 (R) | 14.4 ± 3.6 (S) |
| Aust-R3 | Australia | 0.2 ± 0.1 (R) | 2.5 ± 0.4 (R) | 18.1 ± 5.4 (S) |
| C1 | China | 0.2 ± 0.1 (R) | 2.9 ± 1.0 (R) | 29.9 ± 3.1 (S) |
| C2 | China | 1.0 ± 0.7 (R) | 2.6 ± 0.8 (R) | 21.3 ± 2.4 (S) |
| C3 | China | 0.2 ± 0.1 (R) | 5.3 ± 2.4 (MR) | 25.4 ± 3.3 (S) |

TABLE 1-continued

Comparison of the resistance spectrum of Xa31and Xa21 to different Xoo strains in IR24 genetic background[a]

| Strain | Origin | IRBB31 | IRBB21 | IR24 |
|---|---|---|---|---|
| C4 | China | 16.6 ± 3.7 (S) | 1.3 ± 0.3 (R) | 18.2 ± 2.5 (S) |
| C5 | China | 0.3 ± 0.1 (R) | 1.2 ± 0.5 (R) | 16.6 ± 3.5 (S) |
| C6 | China | 0.3 ± 0.1 (R) | 1.3 ± 0.3 (R) | 22.9 ± 3.0 (S) |
| C7 | China | 0.2 ± 0.1 (R) | 1.9 ± 0.4 (R) | 21.9 ± 4.4 (S) |
| GD1358 | China | 0.2 ± 0.0 (R) | 2.7 ± 0.8 (R) | 13.7 ± 3.3 (S) |
| HB17 | China | 4.5 ± 3.9 (MR) | 2.2 ± 0.6 (R) | 20.7 ± 3.3 (S) |
| HB21 | China | 0.3 ± 0.2 (R) | 2.2 ± 0.4 (R) | 33.4 ± 2.1 (S) |
| HLJ72 | China | 1.3 ± 1.0 (R) | 1.9 ± 0.5 (R) | 21.8 ± 3.8 (S) |
| JS49-6 | China | 0.4 ± 0.1 (R) | 1.8 ± 0.4 (R) | 21.7 ± 4.1 (S) |
| LN57 | China | 0.1 ± 0.0 (R) | 0.2 ± 0.1 (R) | 25.2 ± 4.5 (S) |
| NX42 | China | 0.4 ± 0.1 (R) | 2.0 ± 0.8 (R) | 20.4 ± 3.4 (S) |
| ZHE173 | China | 17.2 ± 3.4(S) | 1.6 ± 0.6 (R) | 21.7 ± 3.7 (S) |
| CIATI185 | Columbia | 0.2 ± 0.2 (R) | 2.0 ± 1.0 (R) | 13.8 ± 3.3 (S) |
| A3842 | India | 0.2 ± 0.1 (R) | 7.0 ± 2.7 (MS) | 20.9 ± 2.8 (S) |
| A3857 | India | 0.2 ± 0.1 (R) | 3.0 ± 1.0 (R) | 24.2 ± 2.7 (S) |
| IXO56 | Indonesia | 0.2 ± 0.1 (R) | 4.4 ± 1.9 (MR) | 28.8 ± 5.0 (S) |
| H75373 | Japan | 2.4 ± 1.2 (R) | 2.1 ± 0.4 (R) | 23.3 ± 3.4 (S) |
| T7174 | Japan | 0.5 ± 0.5 (R) | 2.0 ± 0.7 (R) | 27.6 ± 3.2 (S) |
| JW89011 | Korea | 5.7 ± 3.5 (MR) | 21.8 ± 2.4(S) | 28.6 ± 4.6 (S) |
| K202 | Korea | 24.1 ± 2.8 (S) | 3.1 ± 1.6 (MR) | 19.0 ± 3.4 (S) |
| NXO260 | Nepal | 0.2 ± 0.1 (R) | 5.6 ± 1.6 (MR) | 18.0 ± 3.3 (S) |
| PXO86 (R2) | Philippines | 0.1 ± 0.0 (R) | 1.3 ± 0.6 (R) | 20.0 ± 3.5 (S) |
| PXO79 (R3) | Philippines | 0.2 ± 0.1 (R) | 1.7 ± 0.5 (R) | 14.4 ± 3.2 (S) |
| PXO71 (R4) | Philippines | 5.5 ± 3.5 (MR) | 2.6 ± 0.8 (R) | 20.8 ± 4.1 (S) |
| PXO113 (R4) | Philippines | 1.5 ± 0.3 (R) | 2.6 ± 1.1 (R) | 14.8 ± 2.2 (S) |
| PXO112 (R5) | Philippines | 0.1 ± 0.0 (R) | 3.4 ± 0.6 (MR) | 14.9 ± 3.5 (S) |
| PXO99 (R6) | Philippines | 0.2 ± 0.1 (R) | 1.3 ± 0.3 (R) | 26.1 ± 3.8 (S) |
| R-7 | Thailand | 1.6 ± 0.7 (R) | 2.3 ± 0.6 (R) | 12.9 ± 2.7 (S) |
| 2 | Thailand | 9.6 ± 3.7 (S) | 12.8 ± 3.1 (S) | 25.7 ± 5.7 (S) |

[a]Six-weeks-old plants were inoculated with *X. oryzae* pv. *oryzae*. For each strain, at least sixteen leaves from four individual plants were inoculated. The lesion length is the average of 16 infected leaves. The standard deviation of the mean is indicated.
[b]Lesion length (cm).
[c]Standard deviation.
[d]R, resistant, 0 cm ≤ lesion length ≤ 3.0 cm; MR, moderately resistant, 3.0 cm < lesion length ≤ 6.0 cm; MS, moderately susceptible, 6.0 cm < lesion length ≤ 9.0 cm; S, susceptible, lesion length > 9.0 cm.

Example 2

Identification of Molecular Markers Linked to Xa31 Locus and Genetic Mapping

Both RAPD (Williams et al. 1990) and AFLP (Vos et al. 1995) techniques were used to screen for Xa31-linked markers. To detect more polymorphism in both BSA and individual screen of RAPD products, we added [$^{33}$P-α]dCTP to the PCR mix for labeling RAPD products and separated the RAPD products in a 4.5% polyacrylamide sequencing gel. About 20-50 bands ranging in size from 100 bp to 1500 bp could be detected for each primer. In total, 1200 random primers (Operon Technologies) were screened, and 144 primers were found to detect polymorphism between resistant and susceptible pool, However, after confirmation of RAPD products with individual DNA samples, only random primer BE05 was found to reproducibly detect a polymorphic band between resistant and susceptible individuals (data not shown). The polymorphic band, designated as RM2, is a resistant allele-associated polymorphic DNA. For some unknown reasons, RM2 was not detectable in the BE05-RAPD products of all parents involved in the introgression (*O. minuta* Acc. 101141, IR31917-45-3-2, IR24 and CO39). RM2 was successfully cloned from the dried polyacrylamide gel into pGEM-T vector (Promega, Wisc.) and the DNA sequence was revealed to be 336-bp in length. RM2 was then developed into the corresponding RFLP probes for linkage analysis with Xa31 mapping population.

Figure 4:
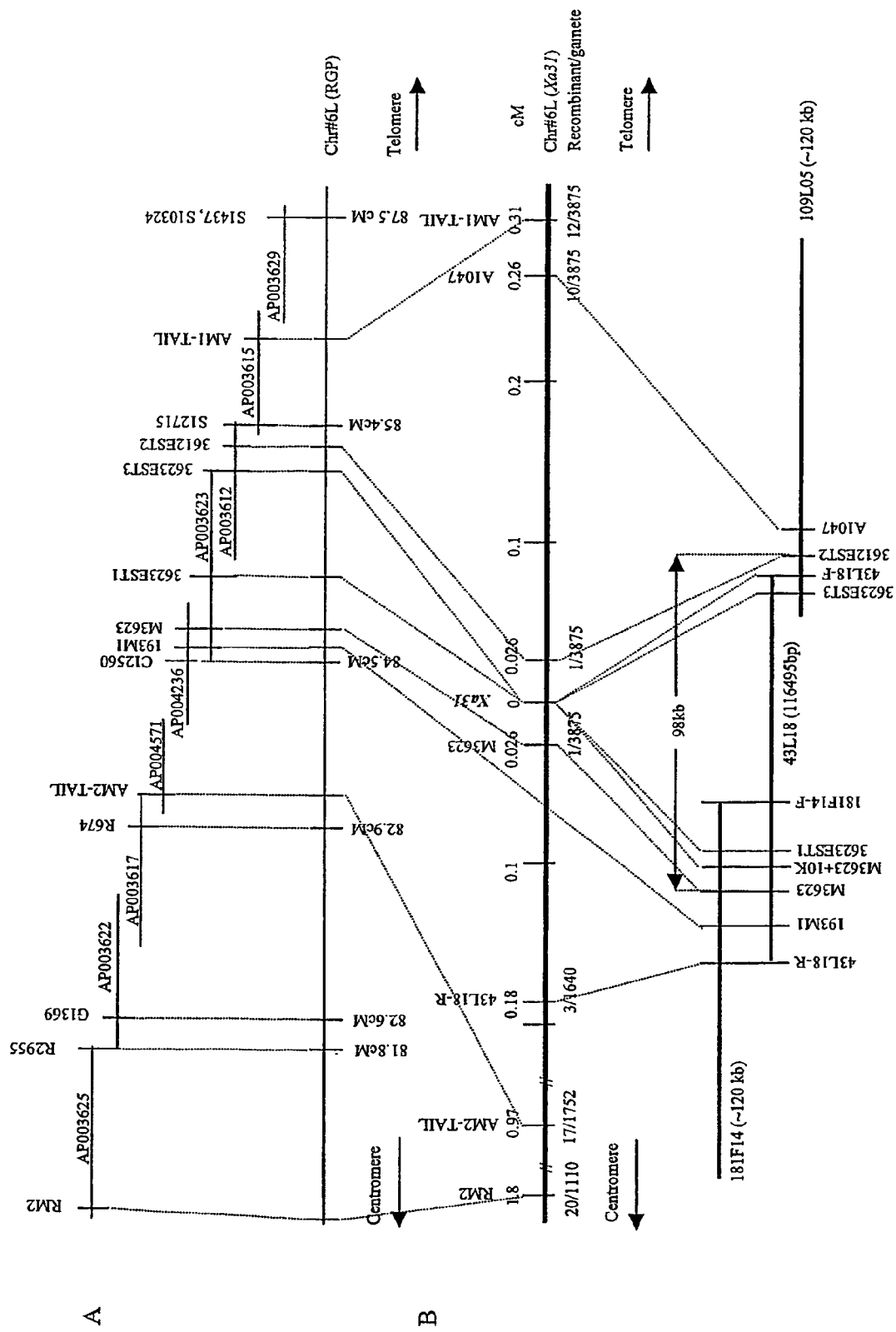
FIGS. 4A and 4B show genetic and physical maps of the Xa31 locus.

Southern hybridization revealed that RM2 has at least four copies in cultivated rice genome and one of the copies, which was non-parental to any of the parents, was linked to the Xa31 locus (data not shown). To determine accurately the genetic distance between RM2 and Xa31, 837 plants consisting of 1110 gametes from the Xa31 mapping population were screened with RM2 and 20 RM2 recombinants were identified. Thus it was confirmed that RM2 is 1-8 cM from the Xa31 locus (FIG. 4B). To identify markers between RM2 and Xa31 or markers on the other side of RM2 corresponding to the Xa31 locus, we performed AFLP analysis with individual DNA samples from 6 Xa31 segregating populations derived from initial 6 available RM2 recombinants in IR24 genetic background. A parallel experiment was also carried out with individual DNA samples from an Xa31 segregating population in CO39 genetic background (see materials and methods). All 64 pairwise combinations of EcoRI and MseI primers were used to screen for polymorphism between individuals. Two pairwise combinations of EcoRI and MseI primers, E-AT/M-CAA and E-AT/M-CTA, were found to detect polymorphic bands between individuals The two polymorphic bands were designated as AM1 and AM2, respectively. AM1 was detectable in all resistant individuals but not in susceptible individuals in both the experiments (data not shown). AM2 was detected in resistant individuals from CO39 segregating population as well as in the six resistant individuals derived from two RM2 recombinants (data not shown), which suggests that AM2 has complemented 2 of the 6 RM2 recombinants and presumably located between RM2 and Xa31. AM1. AM1(130-bp) or AM2 (212-bp) cloned from the two genetic backgrounds turned out to be identical.

Since both AM1 and AM2 were too short to be used as probes for RFLP analysis and AM2 contains some repetitive sequences, we then used TAIL-PCR to obtain the flanking sequence of the two putative AFLP markers. A 1059-bp DNA fragment was isolated with the nested primer A1F3 and the arbitrary degenerate primer AD3. The 1059-bp fragment has only single copy in rice genome and showed polymorphism between the resistant allele and susceptible allele when digested with restriction enzyme HaeII or AvaI. The 1059-bp fragment was then designated as AM1-TAIL. Similarly, a 1238-bp DNA fragment was amplified with the nested primer A2F3 and AD3. However, only 1081-bp of the 1238-bp DNA fragment shows single copy in the rice genome. The 1081-bp DNA fragment designated as AM2-TAIL, was then amplified from the TAIL-PCR product with primers AM2-TAIL-F and AM2-TAIL-R (Table 2). AM2-TAIL showed polymorphism between resistant and susceptible alleles when digested with restriction enzyme SpeI or XbaI.

Genetic distance of AM1-TAIL or AM2-TAIL to Xa31 was determined by genetic linkage analysis of the two makers to the Xa31 locus in the mapping population. Totally, twelve recombinants were identified by AM1-TALL from all of the 2369 individuals consisting of 3875 gametes. The genetic distance between AM1-TAIL and Xa31 was 0.31 cM (FIG. 4B). Seven recombinants were identified by AM2-TAIL from 354 individuals consisting of 642 useful gametes. In the meantime, ten recombinants were identified independently from the 20 RM2 recombinants. Thus, seventeen recombinants were obtained at the AM2-TAIL locus and the genetic distance between AM2-TAIL and the Xa31 locus was assessed to be 0.97 cM [17 recombinants identified from 1752 (1110+642) gametes] (FIG. 4B). Because both AM1-TAIL and AM2-TAIL could complement all of the each other's recombinants (data not shown), the two markers should flank the Xa31 locus (FIG. 4B). FIGS. 4A and 4B show a high-resolution genetic map and BAC contig of RGP at the syntenic locus of Xa31 on the long arm of rice chromosome 6 (A) and of the Xa31 locus generated in this study (B). Genetic distances are given in cM corresponding to the genetic position on rice chromosome 6. The accession numbers of BAC sequence of RGP are marked on each BAC. The overlaps of RGP BAC inserts are not drawn to scale. The number of recombinants and gametes in genetic mapping is indicated under each marker. The overlaps between BAC inserts and the size of each BAC insert in 13 are drawn to scale. The dotted vertical lines mark the relative positions of the corresponding markers. The 98 kb region comprising the Xa31 locus is indicated.

Example 3

Integration of AM1-TAIL and AM2-TAIL into the Rice Linkage Map

Figure 3:
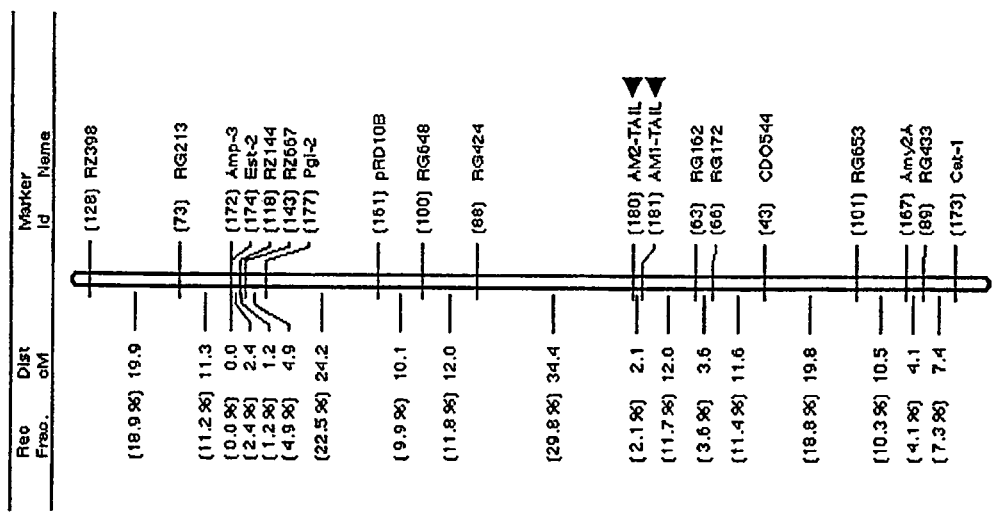
FIG. 3 shows the mapping of Xa31-linked markers, AM1-TAIL and AM2-TAIL.

AM1-TAIL and AM2-TAIL were used to map Xa31 on the rice linkage map. For this purpose, genomic DNA from the two parents (IR64 and Azucena) of the DH mapping population (Huang et al. 1994) was digested by 30 different restriction enzymes and blotted for parental survey of polymorphism using AM1-TAIL and AM2-TAIL as RFLP probes. Both the markers showed detectable polymorphism for at least one of the 30 restriction enzymes tested. The two markers were roughly mapped on the long arm of rice chromosome 6 between marker RG424 and RG162 with AM1-TAIL as the distal marker and AM2-TAIL as the proximal marker (FIG. 3). The genetic distance between AM1-TAIL and AM2-TAIL was 2.1 cM (FIG. 3), which was comparable to 1.28 cM (0.31 cM+0.97 cM) obtained from the Xa31 genetic mapping population (FIG. 4B). The genetic distance between RG424 and AM2-TAIL was 34.4 cM and it was 12.0 cM between AM1-TAIL and RG162 (FIG. 3). The genetic interval between RG424 (70.4 cM on chromosome 6) and RG162 (104.6 cM on chromosome 6) was 34.2 cM on the Cornell map, which covers almost half of the long arm of chromosome 6 (McCouch et al. 2001). FIG. 3 shows the mapping of Xa31-linked markers, AM1-TAIL and AM2-TAIL, to the rice genetic linkage map using MAPMAKER2.0 (Lander et al., 1987). AM1-TAIL (arrowed) and AM2-TAIL (allowed) are mapped on rice chromosome 6. Other markers on the map are RFLP markers from S. McCouch (Cornell University). The numbers on the left indicate recombination fraction and genetic distance (cM), respectively. The maximum-likelihood map order for markers was determined with a LOD score threshold of 3.0, and all map distances (cM) are reported in Kosambi units.

Example 4

Landing of Xa31-linked Markers on Rice Genome and Fine Genetic Mapping

Since the genomic sequence of chromosome 6 of *O. sativa* cv. Nipponbare was accessible from RGP website and both AM1-TAIL and AM2-TAIL are single copy in rice genomo, we then performed fine mapping of the Xa31 locus by landing the two markers on rice genomic sequence. Firstly, we used the two markers to BLAST the Unfinished High Throughput Genomic Sequences (htgs) of rice. AM1-TAIL could hit the sequence of AP003615 of RGP PAC clone P0486H12 from chromosome 6 (Identities=999/1008 (99%) for position 19-1026 on AM1-TAIL) AM2-TAIL picked up the sequences of AP004571 (RGP PAC clone P065Z05), AP004327 (Monsanto BAC clone OJ1378_E04), AP003941 (Monsanto BAC clone OJ1111_E06) and AP003617 (RGP PAC clone P0502H06) (Identities=412/416 (99%) for position 161-575 and 462/494 (93%) for position 589-1081 on AM2-TAIL). Sequence analysis indicated that the latter four 3BAC or PAC clones are overlapping clones at the AM2-TAIL locus on chromosome 6 (data not shown). Then-we downloaded the genomic sequence as well as genetic makers flanked by AM1-TAIL and AM2-TAIL from RGP website. A genetic map and a physical BAC/PAC contig of the Xa31 locus were generated as shown in FIG. 4A. The physical size between AM1-TAIL and AM2-TAIL was 480-kb on the RGP BAC/PAC contig. To confirm the genetic map, an RGP marker, R674 kindly provided by T. Sasaki of RGP), was selected for linkage analysis. Two mapping populations, one containing 32 resistant BC4F1 individuals and another 37 resistant BC2F2 individuals including three AM2-TAIL recombinints, were used for RFLP analysis. Hybridization results indicated that the resistance-associated allele of R674 always co-segregated with the resistance individuals except for the three recombinants shared with AM2-TAIL. Linkage analysis with RM2 and AM2-TAIL recombinants also showed that 19 recombinants were located at R674 locus, among which 17 recombinants were shared with AM2-TAIL and two more crossovers (recombinants) occurred within the 20-kb (RGP physical distance) region between P674 and AM2-TAIL.

Recombinants identified by AM1-TAIL and AM2-TAIL and the available genomic sequence of RGP between them enabled us to perform fine genetic and physical mapping of the Xa31 locus based on RGP genetic and physical maps. To meet these goals, we designed markers based on available EST (expressed sequence tag) information from Genbank as well as unique sequences of the region in the rice genome. The putative markers were amplified from Nipponbare and surveyed for polymorphism among the Xa31 parents. More than 30 putative markers were tried and four markers were finally selected for fine genetic mapping of Xa31 with primers shown in Table 2. Marker 3612EST2 complemented 11 of the 12 AM1-TAIL recombinants and M3623 complemented 16 of the 17 AM2-TAIL recombinants. We further confirmed that the two markers are closely linked to Xa31 by screening the mapping population with RFLP analysis. M3623 is the closest proximal marker while 3612EST2 is the closest distal marker as the two Xa31 flanking markers could complement each other's recombinants. Two recombinants, 24-2-2-943 and 24-10-3-2-147, were identified to be the closest to the Xa31 locus by the proximal marker M3623 and the distal marker 3612EST2, respectively (data not shown). The two recombinants were finally complemented respectively by two EST markers 3623EST1 and 3623EST3 (Table 2), which locate within the interval between M3623 and 3612ES17 (FIG. 4A). The most closely liked RGP markers to the Xa31 locus are the proximal marker C12560S and the distal maker S12715, which flank 0.9 cM genetic interval (FIG. 4A).

In conclusion, Xa31 was mapped to a genetic interval of 0.052 cM (2 recombinants identified from 3875 gametes) between M3623 and 3612ES12 with strong recombination suppression at the locus, and the physical size of the syntenic region on the genome of Nipponbare is 146-kb.

TABLE 2

List of the molecular markers developed in this study

| Marker | PCR primers (5'-3') | | Size (bp) | Enzyme[a] |
|---|---|---|---|---|
| RM2 | NA[b] | | 336[c] | HindIII |
| AM1-TAIL | NA[b] | | 1059[d] | AvaI or HaeII |
| AM2-TAIL | F: TAGCTAAATAAAAGCAATTTTACGA | (SEQ ID NO: 6) | 1081[c] | XbaI or SpeI |
| | R: GCCCTTACATATCGATGTTTATTG | (SEQ ID NO: 7) | | |
| M3623 | F: TGTGCAATGCAGGATTTCAGTTACT | (SEQ ID NO: 8) | 964[c] | PstI |
| | R: TTTCACCTGCATAATGCAAAAGCTAA | (SEQ ID NO: 9) | | |
| 3623EST1 | F: CTGCATCCATGCCGGTGGCCG | (SEQ ID NO: 10) | 631[c] | NdeI |
| | R: AAACGTCACATGAAGACTCCAATTGT | (SEQ ID NO: 11) | | |
| 3623EST3 | F: AGGGATGTCGAGATGAGAGCTTC | (SEQ ID NO: 12) | 1230[c] | EcoRI |
| | R: GGTGTCCTTCTTTACGGGCCTCC | (SEQ ID NO: 13) | | |
| 3612EST2 | F: GCTGTGAAGTGCCGGGTGTCC | (SEQ ID NO: 14) | 1197[c] | BclI |
| | R: TGGACAGGACGATGCCGGTGG | (SEQ ID NO: 15) | | |
| 193M1 | F: CCCAGCAAGGCCATATCCCGACA | (SEQ ID NO: 16) | 1184[f] | N.A |
| | R: TCCCCGCCTTCGTCTCGCCGT | (SEQ ID NO: 17) | | |

[a]Restriction endonuclease that reveals polymorphism between resistance-associated allele and susceptible-associated allele.
[b]NA, not available. RAPD or TAIL-PCR products were cloned into pGEM-T vector and the inserts were amplified with M13 primers and used as RFLP probes.
[c]DNA fragment excludes the OPERON primer BE05.
[d]DNA fragment excludes AD3 primer.
[e]The PCR products were used as RFLP probes.
[f]probe used for screening BAC library.

Example 5

Generation of an Xa31 Physical Contig, Fine Genetic and Physical Mapping

In order to finally clone the Xa31 gene, a 5× rice-genome-coverage BAC library was constructed with an average insert size of 50-kb. To generate a new marker for BAC library screening, a 1184-bp DNA fragment with putative single copy in rice genome, named 193Ml (FIG. 4A), was designed based on the RGP sequence of AP003623 and amplified from Nipponbare by PCR. Three BAC clones, 181F14 (~120-kb), 33M09((~37-kb) and 99N23((~34-kb), were identified by 191Ml from Xa31 BAC library. BAC ends of the insets from those BAC clones were isolated by TAIL PCR (Liu et al. 1998). BAC fingerprinting showed both 33M09 and 99N23 were encompassed by 181F14 and those two BACs were abandoned in further study. To walk on the rice chromosome, five BAC clones, 43L18, 13O02, 88K09, 105N12 and 133J22 were identified by 181F14 F-end and only one clone, 43L18 was chosen for further study after BAC fingerprinting. In another screening experiment, PST marker 3623EST3 (Table 2 and FIG. 4A) picked up 43L18 and another BAC clone 109L05 Therefore, the contig of the Xa31 BAC inserts was generated containing 181F14 ((~120-kb), 43L18 (116,495-bp) and 109L05 ((~120-kb) (FIG. 4B) In order to obtain more molecular markers as well as gain insight into the Xa31 locus at DNA level, 43L18 and part of 109L05 were completely sequenced by shotgun sequencing strategy. Totally, 1,950,406-bp of overlapped DNA fragments were sequenced and they were aligned into 158,425-bp consensus sequence including 116,495-bp from 43L18.

To further confirm that the Xa31 gene was located within the sequenced region. Molecular markers derived from BAC ends as well as from short-gun clones were used for linkage analysis with the Xa31 mapping population. Three recombinants were identified from 1640 gametes by BAC end marker 43L18-R at proximal side to the Xa31 locus. Ten recombinants were identified from 3875 gametes by shot-gun marker A1047 at distal side to the Xa31 locus and the 10 recombinants were shared by AM1-TAIL. No recombinant was identified by BAC end marker 43L18-P from the mapping population. Shot-gun marker M3623+10K could complement the only one recombinant of M3623. The physical organization of the molecular markers at the Xa31 locus was shown in FIG. 4B. In the Example 4, the Xa31 gene was mapped to the interval between M3623 and 3612EST2. In this study, the physical size of the interval was revealed to be 98 kb in IRBB31 (FIG. 4B).

Example 6

Genetic Complementation and Isolation of an Xa31 Genomic Clone

Gene prediction with the 98-kb interval between M3623 and 3612EST1 showed there was more than 10 putative open reading frames (ORFs) in the interval (data not shown). However, none of the ORFs encoded protein with leucine-rich repeat (LRR), nucleotide binding site (NBS), and/or kinase receptor domains, which are conserved domains in many of the R proteins. Therefore, the isolation of the Xa31 gene would rely on genetic complementation by introducing the genomic clone of Xa31 into susceptible rice variety, such as Taipei 309 or Nipponbare, and looking for resistant phenotype in the transgenic plants.

Figure 5:
FIGS. 5A and 5B show binary vector pC1300 and overlaps of construct inserts in Xa31 complementation study.
Figure 6:
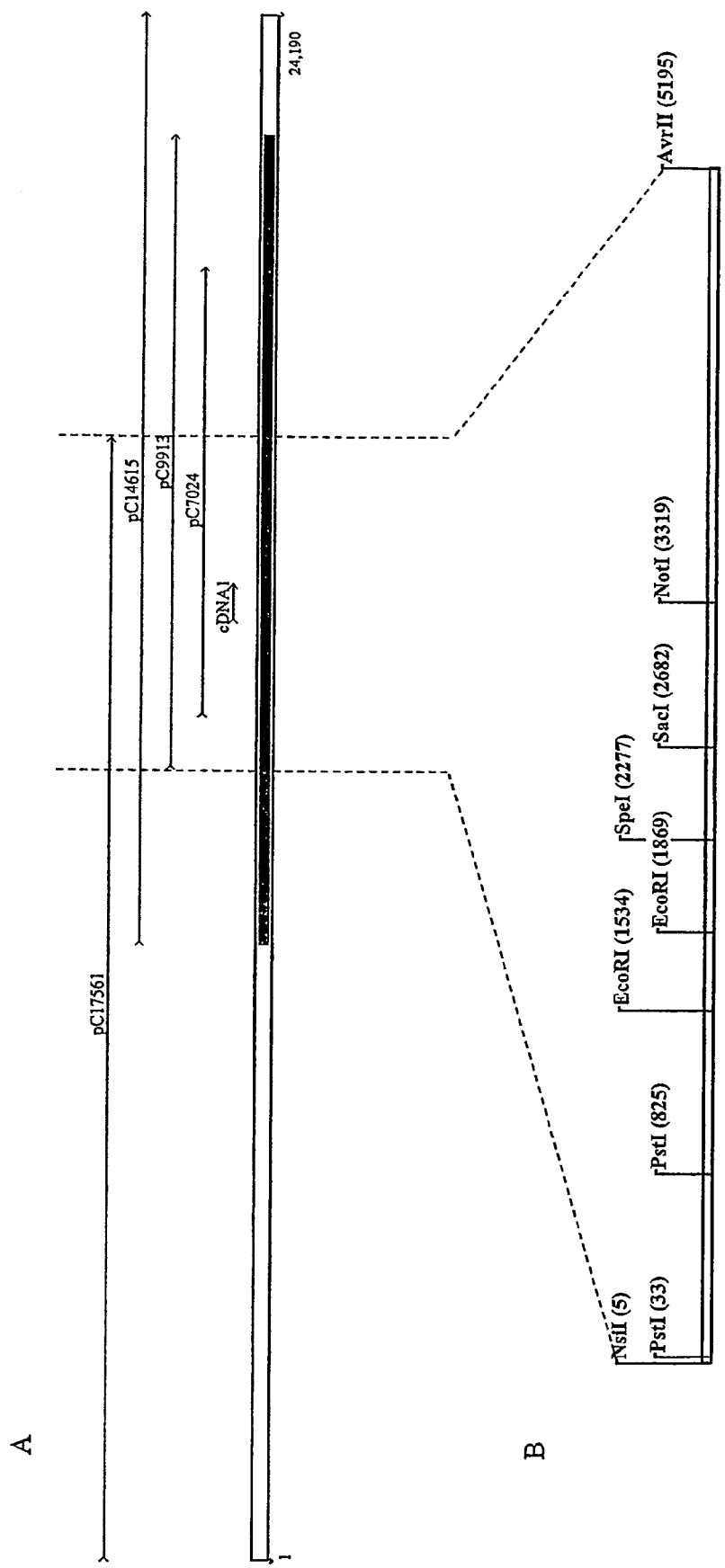
FIGS. 6A and 6B show a Contig of the Xa31 genomic clone.

The 158,425-bp genomic DNA of the Xa31 locus comprised in BAC clones 43L18 and 109L05 was subcloned into binary vector pC1300 (CAMBIA) (FIG. 5A) for *Agrobacterium*-mediated transformation of Taipei 309. Eighteen binary constructs were made and used for rice transformation (FIG. 5B). The size of the inserts in the constructs ranged from 10-kb to 25-kb, The overlapping region between the inserts varied from 4kb to 12-kb with an average size at about 8 kb. The results of blast search for rice EST and gene prediction with the 158,425-bp sequence were also taken into consideration for making the binary constructs. A modified method was used to produce transgenic plants via *Agrobacteria* (Yin et al., 2000). Transformants were evaluated for resistance to Xoo strain PXO99 according to the method described by Kaufman et al (1977). Only healthy and well-developed transgenic plants were used for disease evaluation. Table 3 summarized the results of disease evaluation for the transformants obtained with the 18 binary constructs. Five transformants of pC9913, four transformants of pC14615 and thirty-six transformants of pC17561 showed resistance (R) or moderate resistance (MR) to Xoo PXO99 (Table 3 and FIG. 7). pC14615, pC9913 and pC17561 possessed inserts in a contig of 24190-bp with 5198-bp (SEQ ID NO: 1) in the overlapping region (FIG. 6A).

The homozygous T2 transgenic plants of transformant 1-3 were used for disease evaluation to different Xoo strains. Table 5 summarized the results of disease evaluation with 35 Xoo strains from 11 countries. The Xa31 transgene conferred high resistance to 31 Xoo strains and moderate resistance to 3 Xoo strains, and showed moderately susceptible to one Xoo strain. It was very interesting to find that the Xa31 transgene in Taipei 309 genetic background provided enhanced resistance to the 5 Xa31 compatible strains (1947, C4, ZHE173, K202 and 2) which could infect the 11BB31 (Xa31Xa31) plants in IR24 genetic background. It still remains to be investigated whether this enhanced resistance conferred by the Xa31 transgene in Taipei 309 genetic background resulted from the over-expression of the Xa31 transgene, or other genetic factors present in Taipei 309 which could modify the Xa31 resistance specificity.

Only one of the 60 independent transformants of pC11909 was determined to be resistant to PXO99 in T0 generation and the resistant phenotype of the transformant could be inherited to the next (T1) generation (data not shown). Because the insert in pC11909 has no overlapping region with the 5198-bp fragment (SEQ ID NO. 1), there may be another functional member at the Xa31 locus if the resistant penotype resulted from the transgene possessed in pC11909 or, otherwise, the resistant phenotype resulted from T-DNA insertion or translocation of transposons or retrotransposons during tissue culture. Further genetic characterization of the transformant is in progress.

In summary, genetic complementation of Xa31 phenotype in transgenic plants strongly suggests that the Xa31 gene is located within the 5198-bp (SEQ ID NO: 1) overlapping region of the inserts of the three subclone constructs.

FIGS. 5A and 5B show the binary vector pC1300 and overlaps of construct inserts in Xa31 complementation study. FIG. 5A shows a diagram of binary vector pC1300 (CAMBIA, Canberra, Australia) with restriction digestion sites. BAC 43L18 and 109L05 were digested with proper single or two restriction enzymes and subcloned into the multiple cloning site of the T-DNA of pC1300 to generate binary constructs for rice transformation via *Agrobacterium* AGL1. B. Subclone contig of the Xa31 locus. The overlaps of the inserts generated by Sequencher3.0 are indicated to scale. M3623, A1047 and genomic DNA of the Xa31 locus are included.

FIG. 6A shows the contig of the inserts in binary constructs pC17561, pC14615, pC9913, pC7023 and cDNA 1. The cDNA fragment was drawn with the arrow indicating the direction of transcription. FIG. 6B shows the restriction map of 5198 bp fragment. The long vertical lines flank the 5198 bp fragment and the dotted vertical lines mark the relative position of Nsi I and AvrII. Both of the maps generated by Sequencher3.0 are indicated to scale. All of those R and MR transformants contained at least one copy of T-DNA insertion revealed by Southern analysis (data not shown). The resistant phenotype of the transformants of pC9913 was confirmed in T1 and 12 generation (Table 4 and 5, FIG. 8). Another construct pC7023, which was one of the subclones of pC9913, could also produce 9 resistant T0 plants (Table 3).

Figure 7:
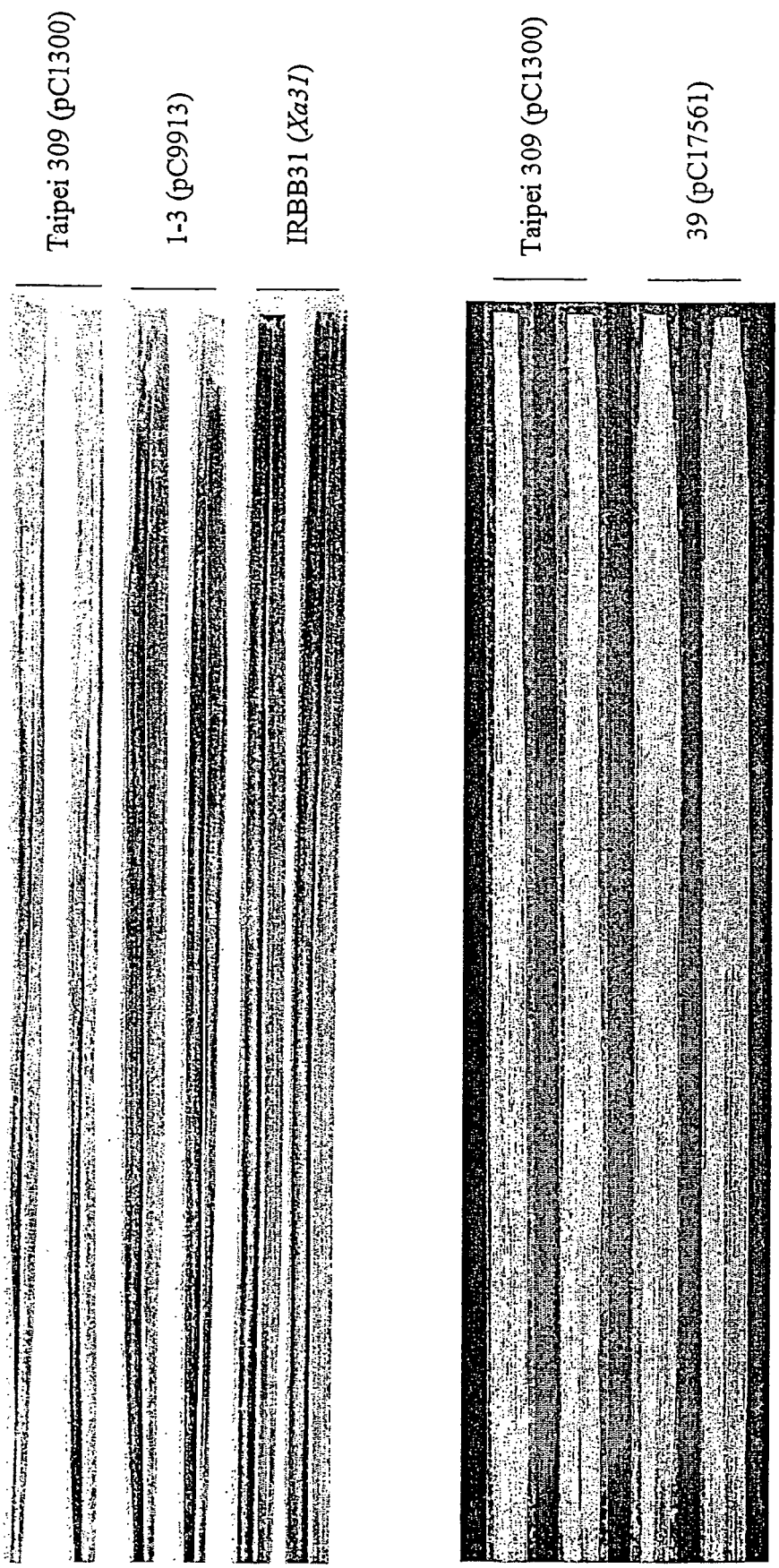
FIG. 7 shows the Phenotype of Xa31 transformants at T0 generation

FIG. 7 shows the phenotype of Xa31 transformants at T0 generation. Eight-week-old rice plants were inoculated with Xoo strain PXO99 using a bacterial suspension with a density of 0.5 at $OD_{600}$. At least 5 fully expanded leaves of a single plant were inoculated using the leaf clipping method (Kauffman et al. 1973) Inoculated plants were maintained in a greenhouse and the lesion length was measured 14 days after inoculation (DAI). Taipei 309 (pC1300), transgenic T0 plants of Taipei 309 wit control binary vector pC1300; 1-3 (pC9913), transgenic T0 plants of Taipei 309 with pC9913; IRBB31, Xa31 near-isogenic line (NIL) in IR24 genetic background; 39(pC17561), transgenic T0 plants of Taipei 309 with pC17561.

Figure 8:
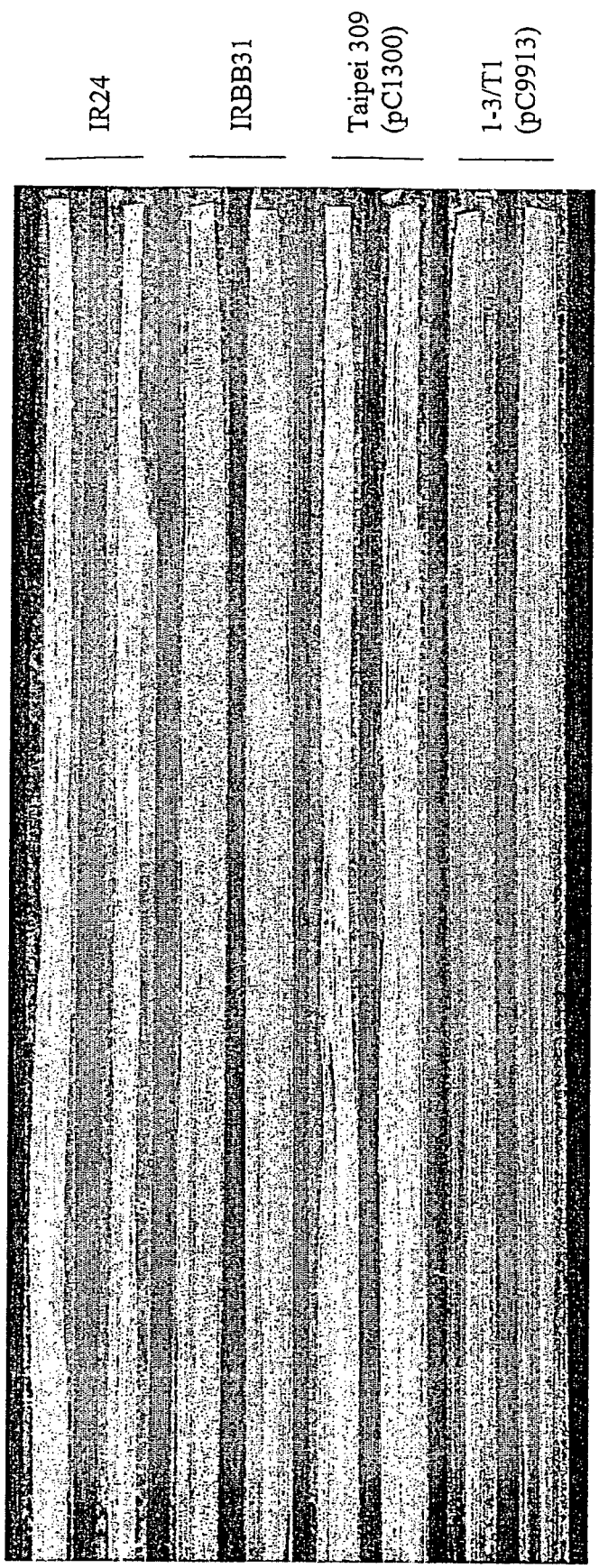
FIG. 8 shows the phenotype of Xa31 transformants at T1 generation

FIG. 8 shows the phenotype of Xa31 transformants at T1 generation. Eight-week-old rice plants were inoculated with Xoo strain PXO99 using a bacterial suspension with a density of 0.5 at $OD_{600}$. At least 5 fully expanded leaves of a single plant were inoculated using the leaf clipping method (Kauffman et al. 1973). Inoculated plants were maintained in a greenhouse and the lesion length was measured 14 days after inoculation (DAI). IRBB31, Xa31 near-isogenic line (NIL) in IR24 genetic background; transgenic T1 plants of Taipei 309 with control binary vector pC1300; 1-3/T1, transgenic T1 plants of Taipei 309 with pC9913.

TABLE 3

Disease evaluation of transgenic T0 plants.

| Constructs[1] | T0 plants | |
|---|---|---|
| | Inoculated plants | R & MR plants[2] |
| pC1300[3] | 11 | 0 |
| pC25052 | 47 | 0 |
| pC15277 | 90 | 0 |
| pC13483 | 92 | 0 |
| pC20805 | 59 | 0 |
| pC13575 | 19 | 0 |
| pC11909 | 60 | 1 |
| pC14615 | 15 | 4 |
| pC9913 | 16 | 5[4] |
| pC17561 | 163 | 36 |
| pC7023 | 93 | 9 |
| pC16991 | 154 | 0 |
| pC15976 | 15 | 0 |
| pC18877 | 48 | 0 |
| pC20384 | 48 | 0 |
| pC 14407 | 115 | 0 |
| PC16794 | 48 | 0 |
| pC17294 | 142 | 0 |
| pC15822 | 122 | 0 |
| pC20013 | 98 | 0 |

[1]Constructs used for complementation study.
[2]R, resistance, lesion length ≦3.0 cm; MR, moderate resistance, 3.0 cm < lesion length ≦ 6.0 cm; S, susceptible, lesion length >9.0 cm.
[3]pC1300 was used for rice transformation as vector control.
[4]Resistant phenotype was confirmed in T1 and T2 generations.

TABLE 4

Phenotypes of transgenic T1 plants inoculated with Xoo PXO99.

| | T1 plants | | | |
|---|---|---|---|---|
| Transformants | Total plants | R[1] | MR[2] | S[3] |
| 1-3 | 70 | 53 | | 16 |
| 2-44 | 55 | 38 | | 17 |
| 3-1 | 30 | 1 | 9 | 20 |
| 4-7 | 22 | 6 | 8 | 8 |
| 14-49 | 37 | 18 | 8 | 11 |

[1]R, resistance, lesion length <3.0 cm.
[2]MR, moderate resistance, 3.0 cm < lesion length ≦ 6.0 cm.
[3]S, susceptible, lesion length >9.0 cm.

TABLE 5

Xa31 gene conferring resistance to multiple Xoo strains in transgenic plants.

| Strain | Origin | Xa31 in TP309 | TP309 |
|---|---|---|---|
| 1947 | Africa | 0.4[c] ± 0.4[d] (R[e]) | 20.1 ± 6.9 (S) |
| Aust-2031 | Australia | 0.5 ± 0.4 (R) | 7.9 ± 2.0 (MS) |
| Aust-R3 | Australia | 0.4 ± 0.3 (R) | 16.2 ± 2.1 (S) |
| C1 | China | 0.3 ± 0.2 (R) | 15.1 ± 2.6 (S) |
| C2 | China | 0.2 ± 0.2 (R) | 12.1 ± 3.5 (S) |
| C3 | China | 0.3 ± 0.3 (R) | 13.3 ± 3.4 (S) |
| C4 | China | 0.3 ± 0.2 (R) | 9.9 ± 2.9 (S) |
| C5 | China | 0.2 ± 0.1 (R) | 4.7 ± 0.6 (MR) |
| C6 | China | 0.3 ± 0.3 (R) | 10.7 ± 1.7 (S) |
| C7 | China | 0.2 ± 0.2 (R) | 9.6 ± 1.6 (S) |
| GD1358 | China | 0.2 ± 0.1 (R) | 5.2 ± 1.7 (MR) |
| HB17 | China | 0.8 ± 0.6 (R) | 29.4 ± 3.6 (S) |
| HB21 | China | 0.7 ± 0.2 (R) | 16.4 ± 4.2 (S) |
| HLJ72 | China | 0.1 ± 0.0 (R) | 10.0 ± 1.4 (S) |
| JS49-6 | China | 0.1 ± 0.2 (R) | 10.8 ± 3.1 (S) |
| LN57 | China | 0.4 ± 0.5 (R) | 20.7 ± 3.3 (S) |
| NX42 | China | 1.1 ± 0.9 (R) | 24.3 ± 3.4 (S) |
| ZHE173 | China | 0.3 ± 0.2(R) | 15.0 ± 2.6 (S) |
| CIAT1185 | Columbia | 0.3 ± 0.4 (R) | 11.6 ± 3.1 (S) |
| A3842 | India | 0.5 ± 0.6 (R) | 22.1 ± 3.0 (S) |
| A3857 | India | 0.2 ± 0.1 (R) | 20.1 ± 3.0 (S) |
| IXO56 | Indonesia | 4.5 ± 3.9 (MR) | 20.2 ± 2.1 (S) |
| H75373 | Japan | 3.0 ± 2.1 (MR) | 20.4 ± 10.5 (S) |
| T7174 | Japan | 5.1 ± 4.4 (MR) | 21.9 ± 1.9 (S) |
| JW89011 | Korea | 2.6 ± 2.4 (R) | 28.7 ± 3.9 (S) |
| K202 | Korea | 6.3 ± 3.2 (MS) | 22.9 ± 3.6 (S) |
| NXO260 | Nepal | 0.3 ± 0.5 (R) | 24.0 ± 2.8 (S) |
| PXO86 (R2) | Philippines | 0.3 ± 0.3 (R) | 16.2 ± 2.4 (S) |
| PXO79 (R3) | Philippines | 0.3 ± 0.6 (R) | 12.0 ± 1.7 (S) |
| PXO71 (R4) | Philippines | 1.8 ± 1.7 (R) | 19.1 ± 3.0 (S) |
| PXO113 (R4) | Philippines | 0.1 ± 0.1 (R) | 16.3 ± 2.7 (S) |
| PXO112 (R5) | Philippines | 0.3 ± 0.4 (R) | 19.8 ± 3.9 (S) |
| PXO99 (R6) | Philippines | 0.3 ± 0.3 (R) | 17.3 ± 3.8 (S) |
| R-7 | Thailand | 0.6 ± 0.7 (R) | 20.2 ± 3.0 (S) |
| 2 | Thailand | 1.7 ± 2.1 (R) | 27.5 ± 3.1 (S) |

[a]Six-weeks-old plants were inoculated with X. oryzae pv. oryzae. For each strain, at least sixteen leaves from four individual plants were inoculated. The lesion length is the average of 16 infected leaves. The standard deviation of the mean is indicated.
[b]homozygous transgenic T3 plants of transformants 1-3 were used for disease evaluation.
[c]Lesion length (cm).
[d]Standard deviation.
[e]R, resistant, 0 cm ≦ lesion length ≦ 3.0 cm; MR, moderately resistant, 3.0 cm < lesion length ≦ 6.0 cm; MS, moderately susceptible, 6.0 cm < lesion length ≦ 9.0 cm; S, susceptible, lesion length > 9.0 cm.

Example 7

Isolation of cDNA clones of the Xa3 candidates and isolation of the corresponding recessive alleles of lie Xa31 gene from IR24. To isolate the cDNA candidate of the Xa31 gene, an Xa31 cDNA library was made for screening for the expressional gene(s) from the 5198-bp fragment of Example 6 (SEQ ID NO:1). A genomic clone of the recessive allele of Xa31 in IR24 was also isolated by PCR using primers derived from the sequence of the resistant allele. DNA sequence alignment of the PCR products showed that a 5131-bp (SEQ D NO: 2) contig was isolated from the sensitive strain IR24. This 5131-bp genomic clone corresponded to the almost full length of the 5198-bp (SEQ ID NO: 1) fragment from IRBB31.

To further isolate the Xa31 cDNA clone, subclones of the 5198-bp fragment were used as probes to screen the Xa31 cDNA library. A 543-bp partial cDNA with a poly(A) of 20-nt was isolated from the cDNA library. To obtain full-length cDNA sequence, a 363-bp cDNA fragment was isolated from Xa31 transgenic plants by 5'RACE. This 363-bp cDNA fragment contained a 313-bp region overlapping with the 543-bp poly(A) cDNA. Thus, the putative full-length cDNA 1 was 593-bp (SEQ ID NO: 3), which was confirmed by amplification of the full-length cDNA 1 by 3'RACE (Table 6 and 7). Comparing cDNA 1 and its genomic clone, no intron was observed within the transcription region. There was only one putative ORF in cDNA 1 which encoded a polypeptide with 113AA (SEQ ID NO: 5). The homologue of cDNA 1 derived from the Xa31 recessive allele, cDNA 3 (SEQ ID NO: 4), was isolated from IR24 by 5' and 3'RACE (Table 6 and 7). cDNA 1 and cDNA 3 were almost identical except that cDNA1 had a longer polyA tail than that of cDNA3.

Northern analysis using dsDNA of cDNA 1 (SEQ ID NO: 3) as the probe indicated the transcripts (cDNA 1 or cDNA 3) at the Xa31 locus were undetectable in both IRBB31 and IR24 without inoculation with Xoo pathogens (data not shown). Trace amount of the transcripts could be detected three 3 DPI in both IRBB31 and IR24 with little difference (data not shown).

Efforts to isolation of cDNA by both screening cDNA library and performing 5' or 3'RACE failed to identify any other expressing region within the 5198-bp (SEQ ID NO: 1) genomic region other than cDNA 1 (SEQ ID NO: 3).

BLASTP/searches showed that no putative conserved domains have been detected within the 113AA (SEQ ID NO: 5). The only similarity found was that the 113 amino acid sequence of SEQ ID NO:5 shows 36.8% or 38.2% of identity at its C-terminal (62-113) to the signal and propetide regions of rat or human neuroendocrine convertase 1 (NEC1) precursor (C3.4.21.93) (data not shown).

The transcripts of the IRBB31 (resistant) and IR24 (susceptible) alleles of the Xa31 gene were identical. However, the differences at the 5' regulation regions were observed with both single nucleotide polymorphism (SNP) and deletions between the two alleles (SEQ ID NO:49, SEQ ID NO:51 and FIG. 9). Two 25-bp tandem repeats were identified at the 20-bp upstream of the putative TATA box in the promoter of the IR24 allele but only one copy of the 25-bp element was found at that of IRBB31 allele. In addition, three nucleotides were deleted at the 3' of the putative TATA box of the IR24 allele if compared to that of the IRBB31 allele. GFP tagging study showed that the functional terminators of the IRBB31 and IR24 alleles were identical (SEQ ID NO:49 and NO:51) (data not shown). FIG. 9 shows a comparison of the promoters at TATA box regions of (IBB31) resistant and (IR24) susceptible alleles of the Xa31 candidate gene (partial). Gaps (indicated in "-") were incorporated to make maximum alignment of the two sequences. Dots below the sequence indicate the difference between IRBB31 and IR24 alleles. Initiation site of transcription is marked as +1 below the sequence. The fist codon of 113AA is indicated in bold case. The first 25-bp repeat is highlighted in italic capital letters while the second 25-bp repeat in italic lowercase. The putative TATA box is underlined.

In summary, the 5198-bp genomic clone (SEQ ID NO:1), cDNA 1 (SEQ ID NO:3), cDNA 3 (SEQ ID NO:4) and 113AA (SEQ ID NO:5), were concluded to be the genomic clone, the cDNA clone and the deduced polypeptide of the Xa31 candidate. The coding regions of the Xa31 candidates wore identical between resistant and susceptible alleles. The Xa31 gene encodes a novel protein showing similarity at its C-terminal to the rat or human NECl protein. The regulation of expression of the Xa31 candidate gene might reside in the 5' upstream or 3' downstream of the coding region

TABLE 6

Primers for isolating putative Xa31(xa31) cDNA fragments by 5'RACE and 3'RACE[a].

| PCR reaction nested | Primer for first-strand cDNA synthesis[b] | Primers for RACE | Primers for PCR |
|---|---|---|---|
| 3'RACE for cDNA 1 | 3'CDS | E4R2/NUP | E4R1/NUP |
| 5'RACE for cDNA 1 (T) | 5'CDS | 3FI/UPM or 128AAF/UPM | 3FI/NUP |
| 3'RACE for cDNA 1 (T) | Oligo-dT-PCR | PW1/PCR-Anchor | PW1/PCR-Anchor |
| 5'RACE for cDNA 3 | 5'CDS | 3F1/UPM | 3F1/NUP |
| 3'RACE for cDNA 3 | Oligo-dT-PCR | E4R2/PCR-Anchor | E4R1/PCR-Anchor |

[a]primer sequences are listed in Table 7.
[b]SMART II A ™ Oligonucleotide, 5'AAGCAGTGGTATCAACGCAGAG-TACGCGGG3' (SEQ ID NO: 18), was added to the reaction of the first-strand synthesis in 5'RACE analysis.

TABLE 7

DNA sequence of primers listed in Table 6

| Primer | DNA sequence (5'-3') |
|---|---|
| 3'CDS | AAGCAGTGGTATCAACGCAGAGTAC(T)30$_{-1}$N (N = A, T, C, or G; N$_{-1}$ = A, C, or G) (SEQ ID NO: 19) |
| E4R2 | CAACCAGCAACGCCACCGAGCC (SEQ ID NO: 20) |
| NUP | AAGCAGTGGTATCAACGCAGAGT (SEQ ID NO: 21) |
| E4R1 | ACCTTGCGTCGCCCTCCTCGTG (SEQ ID NO: 22) |
| 5'CDS | (T)25N$_{-1}$N(N = A, T, C, or G; N$_{-1}$ = A, C, or G) (SEQ ID NO: 23) |

TABLE 7-continued

DNA sequence of primers listed in Table 6

| Primer | DNA sequence (5'-3') |
|---|---|
| 3F1 | CTCCTCAGCAATGGCGGCAGCGA (SEQ ID NO: 24) |
| UPM | CTAATACGACTCACTATAGGGCAAGCAGTGGTATCAACGCAGAGT (long, 10X, 0.4um) (SEQ ID NO: 25) |
| | CTAATACGACTCACTATAGGGC (short; 10X, 2um) (SEQ ID NO: 26) |
| 128AAF | ACACACAGATCCGTACTCAACTCC (SEQ ID NO: 27) |
| Oligo-dT-PCR | GACCACGCGTATCGATGTCGACTTTTTTTTTTTTTTT (SEQ ID NO: 28) |
| PWI | GAGAGCATCAGAGCAAAGTACTCC (SEQ ID NO: 29) |
| PCR-Anchor | GACCACGCGTATCGATGTCGAC (SEQ ID NO: 30) |

GENERAL MATERIAL AND METHODS

Plant materials and growth. The F1 hybrid seeds of 78-1-5 BC2F3 and IR24 were obtained from the International Rice Research Institute (IRRI) (R. Nelson and G. Khush). Plants of 78-1-5 DC2F3 were derived from a cross between *O. sativa* cv IR31917-45-3-2 and *O. minuta* Acc. 10141 (Amante-Bordeos et al. 1992). Disease resistance of the F1 plants was evaluated by inoculation with Xoo strain PXO99 and the highly resistant plants from the backcross 78-1-5-#169 were selected for further backcrosses of isogenic lines. The doubled haploid (DH) mapping population, wild species *O. minuta* Acc. 101141, and other culivars used in the study, i.e., CO39, IR24 and IRBB21, were kindly provided by N. Huang and I. Leung from IRRI. Rice cultivar Taipei 309 was kindly provided by W. Tian from the Institute of Genetics and Development of Chinese Academy of Science, Beijing, China. Rice plants, including those inoculated with Xoo strains, were grown in the greenhouse at a temperature of 26° C. (night) to 32° C. (day) in Singapore.

Xoo strains and bacterial blight inoculation Xoo strains C1, C2, C3, C4, C5, C6, C7 were kindly by Qi Zhang of Chinese Academy of Agricultural Sciences (CAAS). Other Xoo isolates used in this study were kindly provided by J. E. Lech at Kansas State University. Bacterial blight inoculation was carried out using the leaf-clipping method described by Kauffman et al (1973). Briefly, Xoo strains were grown on PSA medium (10 g/l peptone, 10 g/l sucrose, 1 g/l glutamic acid, 16 g/l bacto-agar and pH 7.0) for 2-3 days. The bacterial cells were suspended in sterile water with a density of 0.5 at $OD^{600}$. The bacterial cell suspension was applied to the two youngest fully expanded leaves of each tiller by clipping 5-6 cm from the tip of the leaf using a pair of scissors dipped in the inoculum. Lesion length (LL) was measured two weeks after inoculation. The symptom of disease was ranked as resistant (R, LL≦3.0 cm), moderately resistant (MR, 3.0 cm<LL≦6.0 cm), moderately susceptible (MS, 6.0 cm<LL≦9.0 cm) and susceptible (S. LL>9.0 cm) (Amante-Bordeos et al. 1992).

DNA extraction and Southern hybridization. Rice genomic DNA was extracted from young leaves as described by Dellaporta et al (1984). Approximately 2 μg of rice DNA was digested with an appropriate restriction enzyme and fractionated in a 0.65-0.8% agarose gel by electrophoresis. Southern hybridization was carried out using standard procedures (Sambrook et al, 1989). Labeling of the probes and signal detection were done with the Rediprime™II of Amersham Biosciences.

"Stringent hybridization conditions" are those that (1) employ low ionic strength and high temperature for washing, for example, 0.015M NaCl/0.0015M sodium tartrate/0.1% sodium dodecylsulfate at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SC (0.75M NaCl, 0.075M sodium citrate), 50 mM sodium phosphate (pH 6.8), 0.1% sodium pyrophorphate, 5×Denhardt's solution, sonicated salmon sperm DNA (50 mu g/ml), 0.1% SDS, and 10% dextran sulfate at 42° C., with washes at 42° C. in 0.2×SSC and 0.1% SDS. Alternatively, "stringent hybridization conditions" are those conditions in which a nucleic acid having greater than about 80% homology, preferably greater than about 90% homology, most preferably, greater than about 95% homology to the *R. anatipestifer* OmpA gene will hybridize to that gene. The nucleic acid may be labeled, e.g. using any of the type of labels described above, or alternatively, a labeled reporter nucleic acid that binds to the detection nucleic acid, may be employed. Additionally, other marker techniques as known in the art may be employed.

Randomly Amplified Polymorphic DNA (RAPD) analysis. Ten resistant $F_2$ plants and 10 susceptible $F_2$ plants from an Xa3l segregating population in IR24 genetic background were selected to make resistant pool and susceptible pool respectively for bulk segregant analysis (BSA) (Michelmore et al. 1991). Equal amounts of genomic DNA (10 ng/μl) from each respective individual plant were mixed to form pools. Approximately 10 ng of the pool DNA was used for each RAPD (Williams et al 1990) reaction. Random primers were obtained from Operon Technologies (Alameda, Calif.). The reaction mixture was incubated at as following temperature: 94° C. for 120 s, followed by 40 cycles of 94° C. for 60 s, 37° C. for 45 s, and 72° C. for 90 s. The PCR was terminated following an incubation at 72° C. for 5 min. About 0.1 μl of [$^{33}$P-α]dCTP (3000 Ci/mmol, Amersham Biosciences) was added to each reaction mixture for labeling PCR products. The PCR products were denatured and then separated on a 4.5% polyacrylamide gel using the Sequi-Gen sequencing cell from Bio-Rad (Hercules, Calif.). The dried gel was exposed to Biomax XR film (Eastman Kodak, Rochester, N.Y.) for 2-3 days. Primers that revealed polymorphism between pools were tested further using the 20 individual DNA samples included in the pool. DNA samples from *O. minuta* Acc. 101141, 11R3191745-3-2, IR24 and C039 were also tested for individual RAPD analysis.

Amplified Restriction Fragment Polymorphism (AFLP) analysis. DNA samples from four groups of plants were used for AFLP (Vos et al. 1995) analysis. Groups R1 and S1 consisted of 18 resistant or susceptible individual plants from an $F_2$ segregating population in CO39 genetic background. Groups R2 and S2 contained 18 resistant or susceptible plants from 6 RM2 (RAPD marker 2, also see results section) recombinant segregating populations in IR24 genetic background. AFLP analysis was performed according to the AFLP instruction manual of AFLP™ Analysis System II and AFLP Small Genome Primer Kit (GIBCO BRL). The AFLP preamplified products were obtained through the use of the E-0/M+C primer pairs. For selective amplification; the [$^{33}$P-γ]ATP-labeled EcoRI primers were utilized in combination with MseI primers. All 64 pairwise combinations of EcoRI and MseI primers were used to screen for polymorphism between individual plants of the 4 groups. The amplified DNA fragments were denatured and then separated on a 4.5% polyacrylamide gel using the Sequi-Gen sequencing cell from Bio-Rad. The dried gel was exposed to Biomax XR film for 2-3 days.

Thermal Asymmetric Interlaced PCR (TAIL-PCR). TAIL-PCR was performed according to Liu et al (1995), with the minor modification that 15 supercycles in the secondary reaction and 30 reduced-stringency cycles in the tertiary reaction were performed. The arbitrary degenerate primers are. AD1, NTCGA(G/C)T(A/T)T(G/C)G(A/T)GTT (SEQ ID NO: 31); AD2, NGTCGA(G/C)(A/T)GANA(A/T)GAA (SEQ ID NO: 32); AD3, (A/T)GTGNAG(A/T)AN-CANAGA (SEQ ID NO: 33); AD4, NGTA(G/C)A(G/C)(A/T)GTNA(A/T)CAA (SEQ ID NO: 34); AD5, AG(A/T)GNAG(A/T)ANCA(A/T)AGG (SEQ ED NO: 35); AD6, (G/C)TTGNT A(G/C)TNCTNTGC (SEQ ID NO: 36). The nested primers on BAC vector are: BACF1, ACGTTG-TAAAACGACGGCCAGT (SEQ ID NO: 37); BACF2, GTAATACGACTCACTATA GGGCGA (SEQ ID NO: 38); BACF3, GAGTCGACCTGCAGGCATGCA (SEQ ID NO: 39); BACR1, CTTCCGGCTCGTATGTTGTGTGG (SEQ ID NO: 40); BACR2, GAGCGGATAACAATTTCACA-CAGGA (SEQ ID NO: 41); BACR3, TTAGGTGAGAC-TATAGAATACTCA (SEQ ID NO; 42) (Liu et al. 1998). The nested primers for AM1-TAIL were A1F1 (5'TAACAACAT-GAGAATTACTAATCCG3) (SEQ ID NO: 43), A1F2 (5'CATGTATCCAAGTTCGTAGCTAG3') (SEQ ID NO: 44) and A1F3 (5'TTGGTTTTTTTGAATGAAGGG-TATAT3') (SEQ ID NO: 45); The nested primers for AM2-TAIL were A2F1 (5'AATTCATGCCCACAAGTACAG-TAC3') (SEQ ID NO: 46), A2F2 (5'CTGAAACACAGGAAAAATCCCGTT3') (SEQ ID NO: 47) and A2F3 (5'TGCATAGGCCCTGTTTAGT-TCTAA3') (SEQ ID NO: 48).

Mapping of Xa3l-linked markers on the rice linkage map. A standard mapping population was used for the mapping of Xa3l-linked markers on a rice genetic linkage map. The population consisted of 111 double haploid (DH) lines developed from a cross between the indica variety IR64 and the japonica variety Azucena (Huang et al, 1994). The genetic linkage map constructed in the DH mapping population contains 271 DNA markers. The linkage group or chromosomal locations of the markers identified in this study were determined using the Mapmaker program (Macintosh version 2.0) (Lander et al. 1987). The maximum-likelihood map order for markers was determined with a LOD score threshold of 3.0 and all map distances (cM) are reported in Kosambi units.

BAC library construction. Bacterial Artificial Chromosome (BAC) library of Xa3l was constructed according to the protocols described in details by Wang, et al., (1995). Construction of a rice bacterial artificial chromosome library and identification of clones linked to the Xa-21 disease resistance locus. The Plant J 7:525-533. Briefly, Xa3l homozygous plants (progenies of IR24BC2F2-13-552 (Xa3l/Xa3l)) were grown in a greenhouse for 7-10 days. High-molecular weight (HMW) nuclear DNA was isolated and embedded into low melting agarose plug for partial digestion by HindIII. Partially digested HMW DNA was then size-fractionated using a Pulse-Field Gel Electrophoresis (PFGE) device (CHEF Mapper II, Bio-Rad). Size-fractionated DNA (100-300 kb) was recovered by electroelution (Strong et al., 1997) from low-melting-point agarose gel and ligated to Hind-III digested and dephosphorylated BAC vector pIndigoBAC-5 (EPICENTRE, Madison, Wis. 53713, USA). The ligation mix was electroporated into *E. coli* DH10B cells using the Cell-Porator system (GIBCO-BRL). BAC clones were picked up manually and arrayed in 384-well plates with 60 μl freezing media in each well. BAC clones were cultured at 37° C. for 14-16 hours and stored in an −80° C. freezer. The BAC library consisted of about 50,000 clones with inserts ranging in size from 30-150 kb with the average size at 50 kb. The coverage of this library is at least 5 times equivalent to the rice genome.

Sequencing of BAC DNA. BAC plasmids were sequenced using shotgun method. BAC DNA was purified by running in 0.8% agarose gel and recovered by electroelution (Strong et al., 1997). The purified DNA was sheared by sonication and then fractionated in 1% agarose gel. Size-fractionated DNA (1-1.5 kb) was recovered using gel extraction kit (QIAGEN). The ends of DNA fragments were modified by T4 DNA polymerase and *E. coli* DNA polymerase T Klenow Fragment. The modified DNA fragments were cloned into EcoR V site of pBluescrpt KS (+) (Stratagene) to generate shotgun library. Shotgun plasmids were sequenced from both ends of the inserts with M13 forward or reverse primers using ABI Prism dRhodamine Terminator Cycle Sequencing Ready Reaction Kit (PE Applied Biosystems, Foster City, USA) and an ABI Prism 310 Genetic Analyzer with Data Collection software (PE Applied Biosystem) supplied by the producer.

DNA sequence analysis. The publicly available BAC (Bacterial Artificial Chromosome) or PAC (P1 Artificial Chromosome, Baba et al. 2000) sequences of *O. sativa* cv Nipponbare were downloaded from Rice Genome Sequence Program (RGP) website (http colon//rgp dot dna dot affrc dot go dot jp/cgi-bin/statusdb/stattable.pl?chr=6&lab=RGP) as well as from other available Genbank. DNA sequence was aligned and analyzed using Sequencher 3.0 program. Sequence alignment was also carried out using Pairwise BLAST.

cDNA library construction. To obtain pathogen-induced as well as constitutive mRNA, 6-week-old plants containing homozygous Xa3l gene were inoculated with PXO99 of the Philippines Xoo strains. Three grams of 5-cm leaf tips were harvested at 1, 3, 5, and 7 days after inoculation (DAI) and pooled for RNA isolation with TRIZOL®Reagent (GIBCO BRL). cDNA library was constructed with Uni-ZAP XR insertion vector and kits from STRATAGENE. The cDNA library contained $5.2 \times 10^6$ pfu.

Rapid Amplication of cDNA Ends (RACE). Total RNA was isolated from leaf tissues of IRBB31, IR24 as well as Xa31 transgenic plants 6 days after inoculation (6DAI) with TRIZOL®Reagent (GIBCO BRL). Both 5'- and 3'-rapid amplification of cDNA ends (RACE) were carried out using the SMART™ RACE cDNA Amplification Kit obtained from CLONTECH. The primers used for first-strand cDNA synthesis, 5'RACE and 3'RACE, as well as Nested PCR (second round PCR using 5'RACE or 3'RACE products as templates) are listed in Table 6 and 7.

Transformation. *Agrobacterium*-mediated transformation of Taipei 309 or Nipponbare was carried out according to the method described as Yin et al. (2000). Briefly, vigorously growing embryogenic calli derived from the scutellum of mature embryos was co-cultivated with *A. tumefaciens* strains AGL1 harboring binary constructs. After co-cultivation, the rice tissues were cultured on the $NB_0$ medium containing 250 mg/l cefotaxime, 200 mg/l ampicillin, 2 mg/l 2,4-D and 50 mg/l hygromycin at 26° C. in the dark for 34 weeks. Hygromycin resistant calli were subcultured on fresh selection medium for 2 weeks and then transferred to the $NB_0$ medium containing 1 mg/l 6-BA, 2 mg/l NAA, 5 mg/l ABA and 50 mg/l hygromycin for 3 weeks. Compact, white embryogenic calli showing hygromycin resistance were transferred to the $NB_0$ medium containing 2 mg/l 6-BA, 1 mg/l IAA, 1 mg/l NAA, 1 mg/l KT and 50 mg/l hygromycin and regenerated at 26° C. with a 14-hour light (about 2000 lux) and a 10-hour dark period, Regenerated plantlets were subsequently transplanted to the soil in pots and grown in a greenhouse.

BIBLIOGRAPHY

Amante-Bordeos A, Sitch L A, Nelson R, Dalmacio R D, Oliva N P, Aswidinnoor H, Leung H (1992) Transfer of bacterial blight and blast resistance from the tetraploid wild rice *Oryza minuta* to cultivated rice, *Oryza sativa*. Theor Appl Genet 84:345-354.

Baba T, Katagiri S, Tanoue H, Tanaka R, Chiden Y, Saji S, Hamada M, Nakashima M, Okamoto M, Hayashi M, Yoshiki S, Karasawa W, Honda M, Ichikawa Y, Arita K, Ikeno M, Ohta T, Umehara Y, Matsumoto T, de Jong P J, Sasaki T (2000) Construction and Characterization of Rice Genomic Libraries: PAC Library of Japonica Variety, Nipponbare and BAC Library of Indica Varicty, Kasalath. Bulletin of the NIAR 14:41-49.

Bryan G T, Wu K S, Farrall L, Jia Y, Hershey H P, McAdams S A, Faulk K N, Donaldson O K, Tarcbini R, Valent B (2000) tA single amino acid difference distinguishes resistant and susceptible alleles of the rice blast resistance gene Pi-ta. Plant Cell 12:2033-2045.

Century K S, Lagman R A, Adkisson M, Morlan J, Tobias R, Schwartz K, Smith A, Love J, Ronald P C, Whalen M C (1999) Short communication: developmental control of Xa21-mediated disease resistance in rice. Plant J 20:231-236.

Gao D Y, Xu Z G, Chen Z Y, Sun L H, Sun Q M, Lu F, Hu B S, Liu Y F, Tang LH (2001) Identification of a new gene for resistance to bacterial blight in a somaclonal mutant HX-3 (indica). Rice Genet Newslett 18:66-68.

Dangl J, Jones J D G (2001) Plant pathogens and integrated defence responses to infection. Nature 411:826-833.

Dellaporta S, Wood J, Hicks J (1984) Maize DNA mini prep In: Russell M (Ed) Molecular biology of plants: a laboratory course manual. Cold Spring Harbor Laboratory Press, Cold Spring Harbor, N.Y., pp36-37.

Flor H H (1971) Current status of the gene-for-gene concept Annu Rev Phytopathol 9:275-96.

Goel R K, Gupta A K (1990) Host age in relation to resistance in rice to bacterial blight caused by *Xanthomonas campestris* pv *oryzae*. Trop Agric 67,368-370.

Greenberg J T (1997) Programmed cell death in plant pathogen interactions *Annu. Rev.* Plant Physiol Plant Mol Biol 48:525-545

Huang N, McCouch S, Mew T, Parco A, Guiderdoni E (1994) Development of an RFLP map from a doubled haploid population in rice. Rice Genet Newslett 11:134-137.

Hulbert S H, Webb C A, Simth S M, Sun Q (2001) Resistance gene complexes: evolution and utilization Annu Rev Phytopathol 39:285-312.

Jia Y, McAdams S A, Bryan G T, Hershey H P, Valent B (2000) Direct interaction of resistance gene and avirulence gene products confers rice blast resistance. The EMBO J 19:4004-4014.

Kauffman H E, Reddy A P K, Hsieh S P Y, Merca S D (1973) An improved technique for evaluating resistance to rice varieties of *Xanthomonas oryzae*. Plant Dis Rep 57:537-541.

Khush G S, Angeles E R (1999) A new gene for resistance to race 6 of bacterial blight in rice, *Oryza sativa* L. Rice Genet Newslett 16:92-93.

Kinosbita T (1995) Report of the committee on gene symbolization, nomenclature and linkage groups. Rice Genet Newslett 12:9-153.

Kaku H, Ogawa T (2000) The relationship between browning reaction and bacterial blight resistance gene Xa3 in rice. Rice Genetics Newslett 17:76-77.

Lander E S, Green P, Abrahamson J, Barlow A, Daly M J, Lincoln S E, Newburg L (1987) MAPMAKER: an interactive computer package for constructing primary genetic linkage maps of experimental and natural populations. Genomics 1:174-181.

Lin X H, Zhang D P, Xie Y F, Gao H P, Zhang Q (1996) identification and mapping of a new gene for bacterial blight resistance in rice based on RFLP markers. Phytopathology 86:1156-1159.

Liu Y G, Mitsukawa N, Oosumi T, Whittier R F (1995) Efficient isolation and mapping of *Arabidopsis thaliana* T-DNA insert junction by thermal asymmetric interlaced PCR. Plant J 8:457-463.

Liu Y G, Huang N (1998) Efficient amplification of insert end sequences from bacterial artificial chromosome clones by thermal asymmetric interlaced PCR. Plant Mol Bio Rep 16:175-181.

McCouch S R, Temnykh S, Lukashova A, Cobum J, DelClerkck G, Cartinhour S, Harrinton S, Thomson M, Septiningsih E, Semon M, Moncada P, Li J (2001) Microsatellite markers in rice: abundance, diversity, and applications. In Rice Genetics IV (edited by Khush G S, Brar D S, and Hardy B). Science Publishers, Inc. pl 17-135.

Michelmore R W, Paran 1, Kesseli R V (1991) Identification of markers linked to disease-resistance genes by bulked segregant analysis: rapid method to detect markers in specific genomic regions by using segregating population. Proc Natl Acad Sci USA 88:9828-9832.

Ogawa T (1993) Methods and strategy for monitoring race distribution and identification of resistance to bacterial leaf blight (*Xanthomonas campestris* pv. *oryzae*) in rice. Japan Agric Res Quart 27:71-80.

Ou S H (1985) Rice disease, 2nd edn. Commonwealth Mycology Institate, New England.

Sambrook J, Frisch E, Maniatis T (1989) Molecular Cloning a laboratory manual (2nd edn). Cold Spring Harbor Laboratory Press, Cold Spring Harbor Laboratory, N.Y.

Song W-Y, Wang G-L, Chen L-L, Kim H-S, Pi L-Y, Holsten T, Gardner J., Wang B, Zhai W-X, Zhu L-H, Fauquet C, Ronald P (1995) A receptor kinase-like protein encoded by the rice disease resistance gene, Xa21. Science 270:1804-1806.

Strong S J, Ohta Y. Litman G W, Amemiya C (1997) Marked improvement of PAC and BAC cloning is achieved using electroelution or pulsed-field gel-separated partial digests of genomic DNA. Nucleic Acids Res 25:3959-3961.

Vos P, Hogers R, Bleeker M, Reijans M, van de Lee T, Hornes M, Freijters A, Peleman J, Kuiper M, Zabeau M (1995) AFLP a new technique for DNA fingerprinting. Nucleic Acids Res 23:4407-4414.

Wang, G. L., Holsten, T. E., Song, W. Y., Wang, H. P., Ronald P C (1995) Construction of a rice bacterial artificial chromosome library and identification of clones linked to the Xa-21 disease resistance locus. The Plant J, 7:525-533.

Wang G-L, Song W-Y, Ruan D-L, Sideris S, Ronald P C (1996) The cloned gene Xa21, confers resistance to multiple Xanthomonas oryzae pv. oryzae isolates in transgenic plants. Mol Plant-Microbe Inter 9:850-855.

Wang Z-X, Yano M, Yamanouchi U, Iwamoto M, Monna L, Hayasaka H, Katayose Y, Sasaki T (1999) The Pib gene for rice blast resistance belongs to the nucleotide binding and leucine-rich repeat class of plant disease resistance genes, Plant J 19:55-64.

Williams J G, Kubelik A R, Livak K J, Rafalski J A, Tingey S V (1990) DNA polymorphisms amplified by arbitrary primers are useful as genetic markers. Nucleic Acids Res 18:6531-6535.

Yin Z, Wang G L(2000) Evidence of multiple complex patterns of T-DNA integration into the rice genome. Theor Appl Genet 100:461-470.

Yoshimura S, Yamanouchi U, Katayose Y, Toki S, Wang Z-X, Kono I, Kurata N, Yano M, Iwata N, Sasaki T (1998) Expression of Xa1, a bacterial blight-resistance gene in rice, is induced by bacterial inoculation. Proc Natl Acad Sci USA 95:1663-1668.

Zhang Q, Lin S C, Zhao C L, Wang C L, Yang W C, Zhou Y L, Li D Y, Chen C B Zhu L H (1998) Identification and tagging a new gene for resistance to bacterial blight (Xanthomonas oryzae pv oryzae) from O. rufipogon. Rice Genet Newselett 15:138-142.

What is claimed is:

1. An isolated nucleic acid encoding the polypeptide having the amino acid sequence set forth in SEQ ID NO:5.

2. The isolated nucleic acid of claim 1, wherein the nucleic acid is selected from the group consisting of (i) a nucleic acid having the nucleotide sequence set forth in SEQ ID NO: 1, (ii) a nucleic acid having the nucleotide sequence set forth in SEQ ID NO:3, and (iii) a nucleic acid having the nucleotide sequence set forth in SEQ ID NO:4.

3. A vector which comprises the isolated nucleic acid of claim 1.

4. The vector of claim 3 which farther comprises a plant functional promoter operably linked to said nucleic acid.

5. The vector of claim 4, wherein the promoter is selected from the group consisting of a tissue-specific promoter, a constitutive promoter and an inducible promoter.

6. A vector which comprises the nucleic acid of claim 2.

7. The vector of claim 6 which further comprises a plant functional promoter operably linked to said nucleic acid.

8. The vector of claim 7, wherein the promoter is selected from the group consisting of a tissue-specific promoter, a constitutive promoter and an inducible promoter.

* * * * *